United States Patent
Lee et al.

(10) Patent No.: US 12,239,550 B2
(45) Date of Patent: Mar. 4, 2025

(54) JOINT REPLACEMENT ALIGNMENT GUIDES, SYSTEMS AND METHODS OF USE AND ASSEMBLY

(71) Applicant: Paragon 28, Inc., Englewood, CO (US)

(72) Inventors: Daniel J. Lee, Denver, CO (US); Joseph Dogué, Aurora, CO (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 182 days.

(21) Appl. No.: 17/812,074

(22) Filed: Jul. 12, 2022

(65) Prior Publication Data

US 2022/0339005 A1   Oct. 27, 2022

Related U.S. Application Data

(63) Continuation of application No. 17/304,056, filed on Jun. 14, 2021, now Pat. No. 11,382,765, which is a
(Continued)

(51) Int. Cl.
*A61B 17/46* (2006.01)
*A61B 17/15* (2006.01)
(Continued)

(52) U.S. Cl.
CPC .......... *A61F 2/4606* (2013.01); *A61B 17/15* (2013.01); *A61B 17/7291* (2013.01);
(Continued)

(58) Field of Classification Search
CPC ..................... A61F 2/4606; A61B 17/157
See application file for complete search history.

(56) References Cited

U.S. PATENT DOCUMENTS

| 3,710,473 A | 1/1973 | McElwain |
| 3,750,652 A | 8/1973 | Sherwin |

(Continued)

FOREIGN PATENT DOCUMENTS

| CN | 102405024 | 4/2012 |
| CN | 102770067 | 11/2012 |

(Continued)

OTHER PUBLICATIONS

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

(Continued)

*Primary Examiner* — Andrew Yang
(74) *Attorney, Agent, or Firm* — Heslin Rothenberg Farley & Mesiti P.C.; Jacquelyn A. Graff, Esq.

(57) ABSTRACT

Instruments, devices, systems and methods for maintaining, correcting and/or fusing joint deformities are disclosed. The system includes a first translation mechanism, a second translation mechanism coupled to the first translation mechanism, and a third translation mechanism coupled to the second translation mechanism, and a tower coupled to the third translation mechanism. Methods of assembling and using the alignment guides for maintaining, correcting and/or fusing joint deformities are also disclosed.

18 Claims, 31 Drawing Sheets

Related U.S. Application Data continuation of application No. PCT/US2019/066393, filed on Dec. 13, 2019.

(60) Provisional application No. 62/899,655, filed on Sep. 12, 2019, provisional application No. 62/899,740, filed on Sep. 12, 2019, provisional application No. 62/899,703, filed on Sep. 12, 2019, provisional application No. 62/779,436, filed on Dec. 13, 2018.

(51) Int. Cl.
   *A61B 17/72* (2006.01)
   *A61F 2/42* (2006.01)
   *A61F 2/46* (2006.01)
   *A61B 17/17* (2006.01)
   *A61B 17/68* (2006.01)

(52) U.S. Cl.
   CPC .............. *A61F 2/4202* (2013.01); *A61F 2/46* (2013.01); *A61B 17/17* (2013.01); *A61B 17/1775* (2016.11); *A61B 2017/681* (2013.01); *A61F 2002/4628* (2013.01); *A61F 2002/4687* (2013.01)

(56) References Cited

U.S. PATENT DOCUMENTS

| | | |
|---|---|---|
| 4,899,761 A | 2/1990 | Brown |
| 5,429,121 A | 7/1995 | Gadelius |
| 5,628,750 A | 5/1997 | Whitlock |
| 6,241,729 B1 | 6/2001 | Estes |
| 6,261,296 B1 | 7/2001 | Aebi |
| 6,267,762 B1 | 7/2001 | Millard |
| 6,551,316 B1 | 4/2003 | Rinner |
| 6,673,116 B2 | 1/2004 | Reiley |
| 6,739,068 B1 | 5/2004 | Rinner |
| 6,875,236 B2 | 4/2005 | Reiley |
| 7,025,790 B2 | 4/2006 | Parks |
| 7,153,281 B2 | 12/2006 | Holmes |
| 7,601,154 B2 | 10/2009 | Kuczynski |
| 7,744,601 B2 | 6/2010 | Rosa |
| 8,092,465 B2 | 1/2012 | Metzger |
| 8,439,951 B2 | 5/2013 | Trautwein |
| 8,979,866 B2 | 3/2015 | Patel |
| 9,220,518 B2 | 12/2015 | Neal |
| 9,351,773 B2 | 5/2016 | DiDomenico |
| 9,402,640 B2 | 8/2016 | Reynolds |
| 9,480,571 B2 | 11/2016 | McGinley |
| 9,907,561 B2 | 3/2018 | Luna |
| 9,918,724 B2 | 3/2018 | Luna |
| 9,974,588 B2 | 5/2018 | Stemniski |
| 10,058,335 B2 | 8/2018 | Lee |
| 2001/0029377 A1 | 10/2001 | Aebi |
| 2003/0105467 A1 | 6/2003 | Ralph |
| 2003/0225416 A1 | 12/2003 | Bonvallet |
| 2005/0049603 A1 | 3/2005 | Calton |
| 2006/0142870 A1 | 6/2006 | Robinson |
| 2006/0247646 A1 | 11/2006 | Bihary |
| 2007/0073405 A1 | 3/2007 | Verhulst |
| 2007/0173858 A1 | 7/2007 | Engh |
| 2007/0270783 A1 | 11/2007 | Zumsteg |
| 2008/0082169 A1 | 4/2008 | Gittings |
| 2009/0209964 A1 | 8/2009 | Yeung |
| 2009/0312807 A1 | 12/2009 | Boudreault |
| 2010/0217338 A1 | 8/2010 | Carroll |
| 2011/0208093 A1 | 8/2011 | Gross |
| 2011/0218543 A1 | 9/2011 | van der Walt |
| 2012/0053592 A1 | 3/2012 | Burgi |
| 2012/0101504 A1 | 4/2012 | Habegger |
| 2012/0130376 A1 | 5/2012 | Loring |
| 2012/0130434 A1 | 5/2012 | Stemniski |
| 2012/0232558 A1 | 9/2012 | Berberich |
| 2012/0259335 A1 | 10/2012 | Scifert |
| 2012/0271314 A1 | 10/2012 | Stemniski |
| 2013/0085499 A1 | 4/2013 | Lian |
| 2014/0018931 A1 | 1/2014 | Gillard |
| 2014/0128979 A1 | 5/2014 | Womble et al. |
| 2014/0163563 A1 | 6/2014 | Reynolds et al. |
| 2014/0336658 A1 | 11/2014 | Luna et al. |
| 2015/0182273 A1 | 7/2015 | Stemniski et al. |
| 2015/0265265 A1 | 9/2015 | Hynes et al. |
| 2015/0282952 A1 | 10/2015 | Hes |
| 2015/0305753 A1 | 10/2015 | McGinley et al. |
| 2016/0074053 A1 | 3/2016 | Hutchinson |
| 2016/0135815 A1 | 5/2016 | Loring |
| 2016/0278754 A1 | 9/2016 | Todorov |
| 2017/0079670 A1 | 3/2017 | Haines |
| 2018/0146970 A1 | 5/2018 | Luna et al. |
| 2018/0168826 A1 | 6/2018 | van der Walt et al. |
| 2018/0177511 A1 | 6/2018 | Luna et al. |
| 2018/0177513 A1 | 6/2018 | Stemniski et al. |
| 2018/0243023 A1 | 8/2018 | Stemniski et al. |
| 2018/0263639 A1 | 9/2018 | McGinley |
| 2018/0280038 A1 | 10/2018 | Goble |
| 2018/0317940 A1 | 11/2018 | Stemniski et al. |

FOREIGN PATENT DOCUMENTS

| | | |
|---|---|---|
| EP | 1260183 | 11/2002 |
| FR | 2700462 | 7/1994 |
| JP | 2004130109 | 4/2004 |
| WO | 2005048851 | 6/2005 |
| WO | 2017164862 | 9/2017 |
| WO | 2019091537 | 5/2019 |
| WO | 2020123295 | 6/2020 |
| WO | 2020124047 | 6/2020 |
| WO | 2020124052 | 6/2020 |
| WO | 2020124056 | 6/2020 |

OTHER PUBLICATIONS

Extended European Search Report for European Application No. 19895908.2, Oct. 12, 2022, 7 pages.

JOINT REPLACEMENT ALIGNMENT GUIDES, SYSTEMS AND METHODS OF USE AND ASSEMBLY

CROSS REFERENCE TO RELATED APPLICATIONS

This application is a continuation of U.S. application Ser. No. 17/304,056 filed on Jun. 14, 2021 and entitled Joint Replacement Alignment Guides, Systems and Methods of Use and Assembly, and which will issue as U.S. Pat. No. 11,382,765 on Jun. 12, 2022, which is a continuation of PCT/US2019/066393 filed on Dec. 13, 2019 and entitled Joint Replacement Alignment Guides, Systems and Methods of Use and Assembly, which claims priority benefit under 35 U.S.C. § 119(e) of U.S. Provisional Application No. 62/899,740 filed Sep. 12, 2019 and entitled Joint Replacement Alignment Guides, Systems and Methods of Use and Assembly, U.S. Provisional Application No. 62/899,655 filed Sep. 12, 2019 and entitled Alignment Instruments and Methods for Use in Total Ankle Replacement, U.S. Provisional Application No. 62/899,703 filed Sep. 12, 2019 and entitled Joint Replacement Alignment Guides, Systems and Methods of Use and Assembly, and U.S. Provisional Application No. 62/779,436 filed Dec. 13, 2018 and entitled Joint Replacement Systems and Methods of Use and Assembly, which are incorporated herein by reference in their entireties.

TECHNICAL FIELD

The present disclosure relates generally to general, podiatric, and orthopaedic surgery related to joint deformities. More specifically, but not exclusively, the present disclosure relates to guides, devices, instruments, systems and methods for maintaining, correcting and/or resurfacing joint surfaces.

BACKGROUND OF THE INVENTION

Total ankle replacement (TAR), or ankle arthroplasty, is a surgical procedure to replace deformed and/or damaged articular surfaces of the human ankle joint with a prosthetic joint while preserving the functional range of motion (ROM) of the ankle joint.

Achieving a stable replacement ankle joint that provides for full articulation/motion (e.g., achieving a range of motion of a typical "healthy" ankle joint) can be difficult with currently available TAR surgical procedures and instruments. The currently available systems may not provide for proper sizing and positioning, orientating, aligning of the tibial component with respect to the distal end of a tibia, of the talus component with respect to the proximal end of a talus, or of the insert or spacer therebetween.

Thus, it is an object of the present disclosure to overcome one or more of the above-described drawbacks and/or disadvantages of the currently available systems.

SUMMARY OF THE INVENTION

The present disclosure is directed toward implants, devices and methods for use in maintaining, correcting and/or resurfacing joint surfaces.

In one aspect of the present disclosure provided herein, is an alignment guide system. The system including a first translation mechanism, a second translation mechanism coupled to the first translation mechanism, a tower coupled to a superior surface of the second translation mechanism, and a third translation mechanism coupled to the tower.

In another aspect of the present disclosure provided herein, is method for assembling an alignment guide system. The method includes obtaining a first translation mechanism, a second translation mechanism, a third translation mechanism, and a tower system. The method also includes coupling the first translation mechanism to the second translation mechanism and coupling the tower system to the second translation mechanism. Finally, the method includes coupling the third translation mechanism to the tower system.

In yet another aspect of the present disclosure provided herein, is method for using an alignment guide system. The method includes obtaining an alignment guide system. The alignment guide system includes a first translation mechanism, a second translation mechanism coupled to the first translation mechanism, a tower coupled to a superior surface of the second translation mechanism, and a third translation mechanism coupled to the tower. The method also includes coupling the alignment guide system to a patient's tibia. The method further includes translating the alignment guide system in at least one of a medial-lateral direction, a distal-proximal direction, and a varus-valgus direction.

In yet another aspect of the present disclosure provided herein, is a kit. The kit including a plurality of alignment guide systems as well as alignment attachments, resection attachments and the like for the performing a TAR procedure.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION FOR CARRYING OUT THE INVENTION

Figure 1:
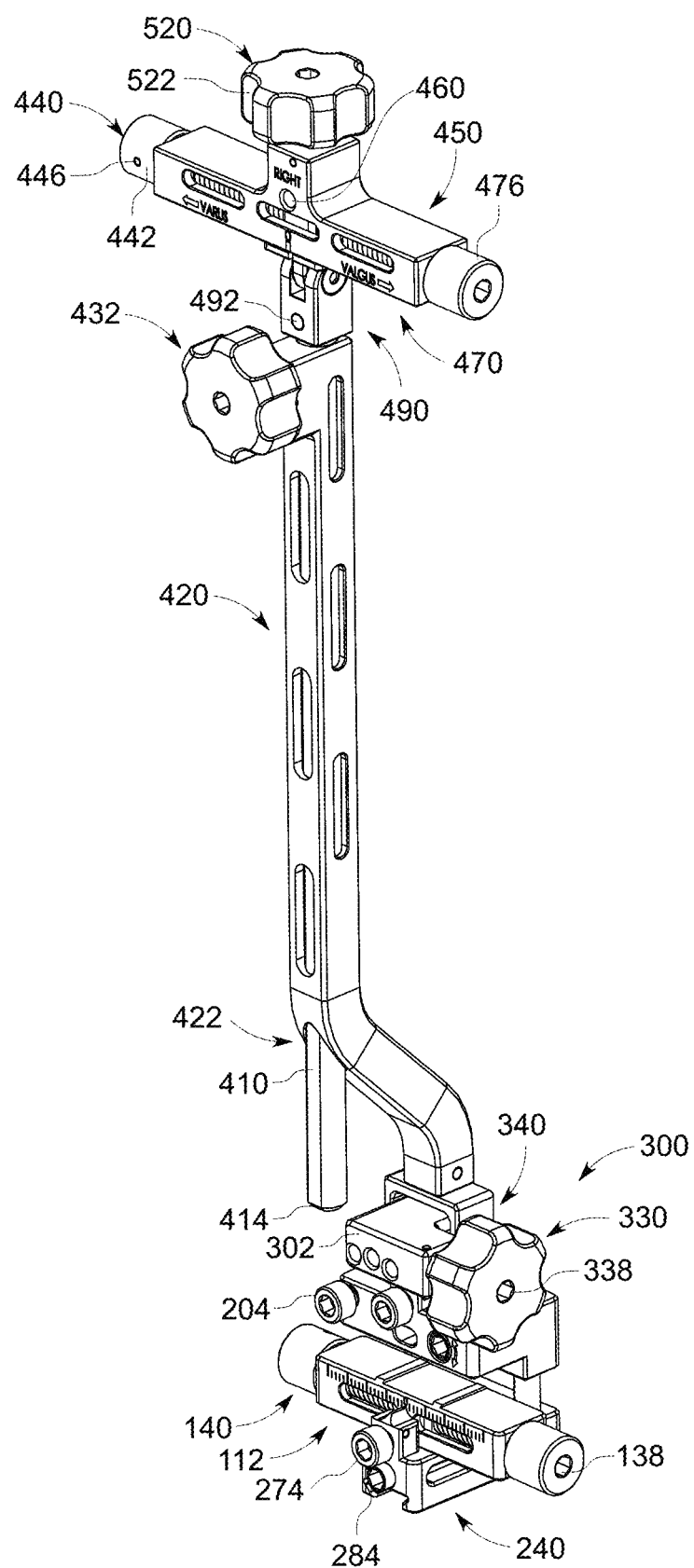
FIG. 1 is a first perspective view of a tibia alignment guide, in accordance with an aspect of the present disclosure.
Figure 2:
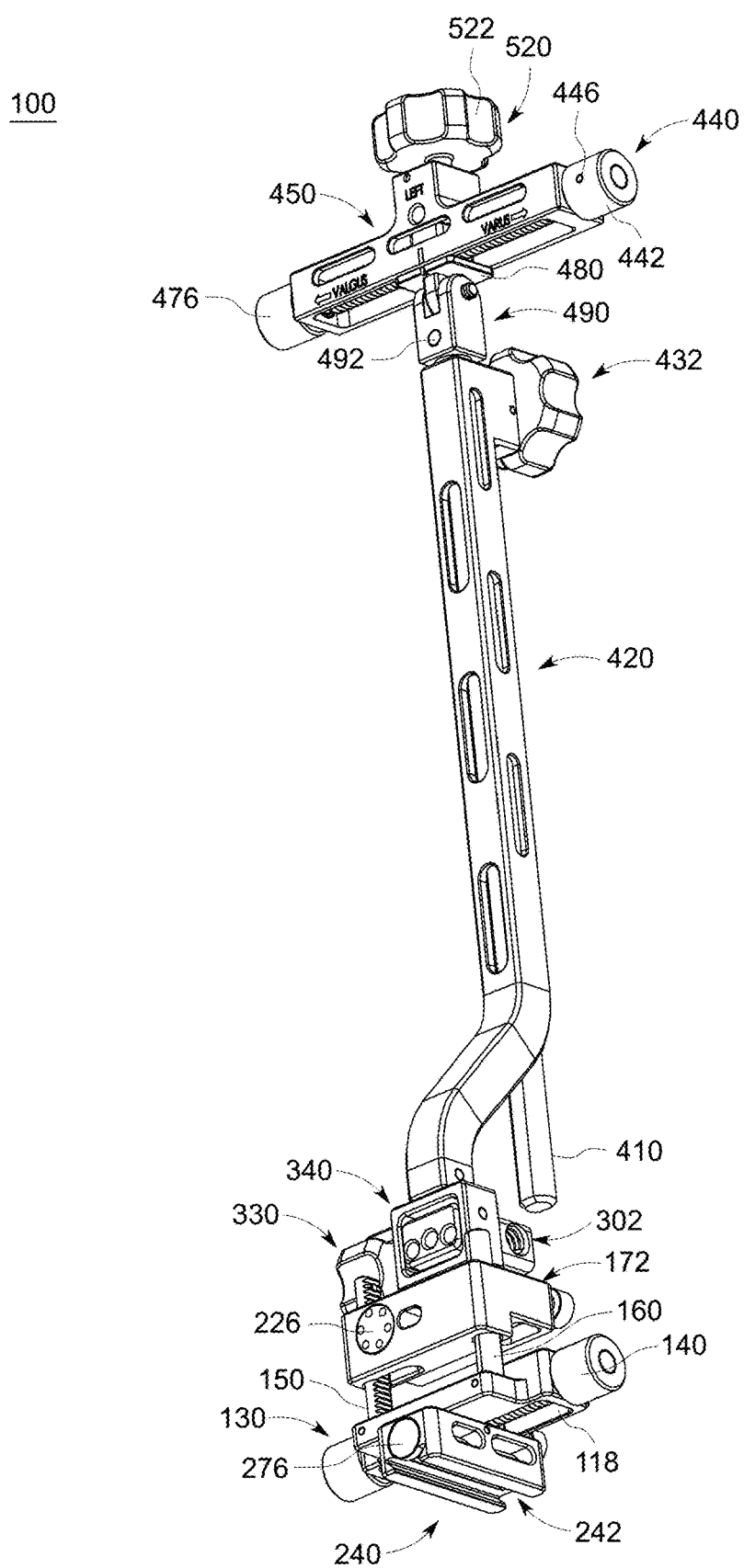
FIG. 2 is a second perspective view of the tibia alignment guide of FIG. 1, in accordance with an aspect of the present disclosure.
Figure 3:
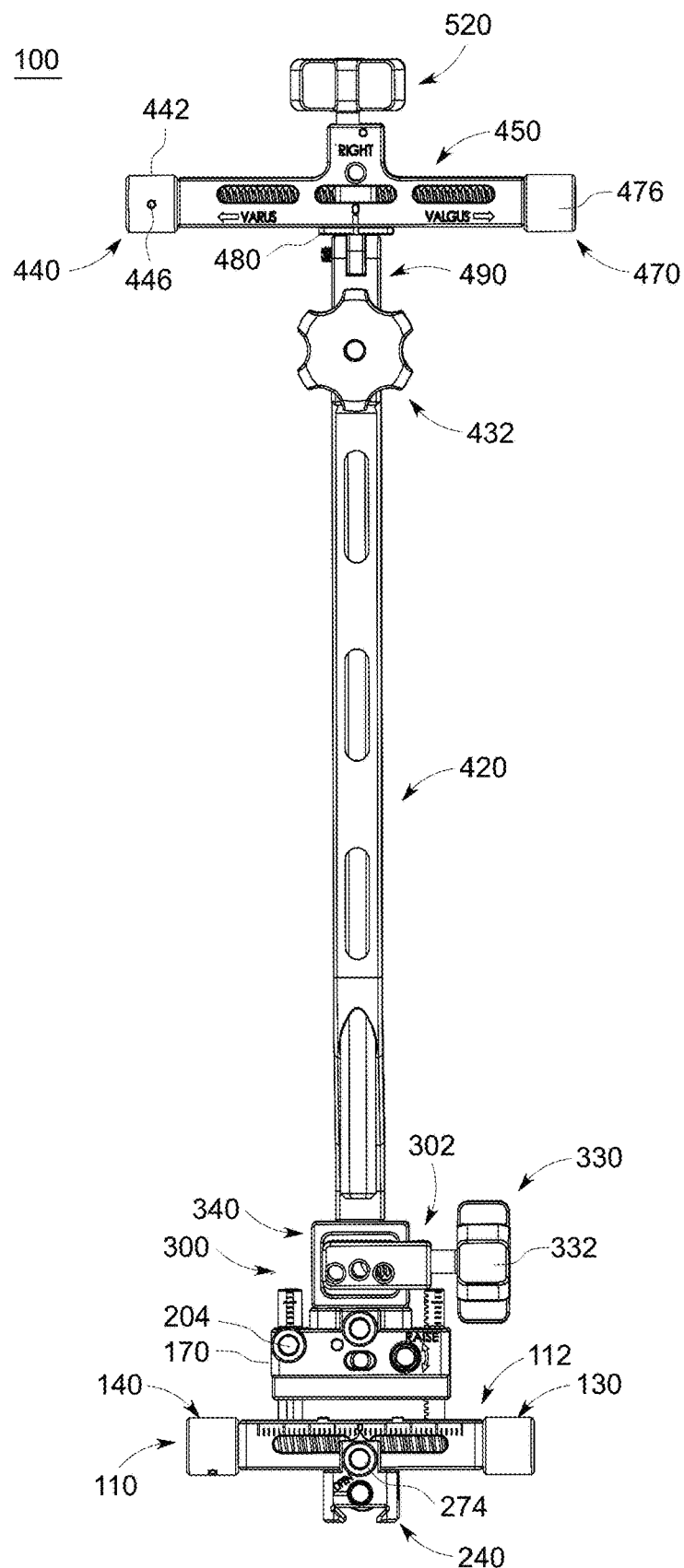
FIG. 3 is a first side view of the tibia alignment guide of FIG. 1, in accordance with an aspect of the present disclosure.

Generally stated, disclosed herein are guides, devices, instruments, systems, and methods for maintaining, correcting and/or resurfacing joint surfaces. Further, methods for using the guides, devices, instruments, systems, and methods for maintaining, correcting and/or resurfacing joint surfaces are discussed.

In this detailed description and the following claims, the words proximal, distal, anterior or plantar, posterior or dorsal, medial, lateral, superior and inferior are defined by their standard usage for indicating a particular part or portion of a bone, instrument, or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-39, the instruments, devices, implants, systems, and methods of using the instruments, devices, implants, and systems for a total ankle replacement (TAR) procedure are shown. The total ankle replacement procedure may include, for example, an alignment procedure, an initial resection procedure, a trialing and chamfer resection procedure, a final trialing and peg preparation procedure, and an implantation procedure.

Referring now to FIGS. 1-39, alignment guides for TAR surgery are shown. A first alignment guide or tibia alignment guide 100 is shown in FIGS. 1-28. As shown in FIG. 1, the alignment guide or full alignment guide 100 includes a first translation mechanism or medial-lateral adjustment member 110, a second translation mechanism or distal-proximal adjustment member 170, a third translation mechanism or varus-valgus adjustment member 440, and a tower 400 coupled to the third translation mechanism 440 on a first end and the second translation mechanism 170 on a second end. The second translation mechanism 170 is movably coupled to the first translation mechanism 110 by distal-proximal translating members 150, 160. The third translation mechanism 440 is moveably coupled to the second translation mechanism 170 by the tower 400. The first and second translation mechanisms 110, 170 may be as described and shown in greater detail in U.S. Provisional Application No. 62/899,703, entitled Joint Replacement Alignment Guides, Systems and Methods of Use and Assembly, which is hereby incorporated by reference in its entirety.

Figure 4:
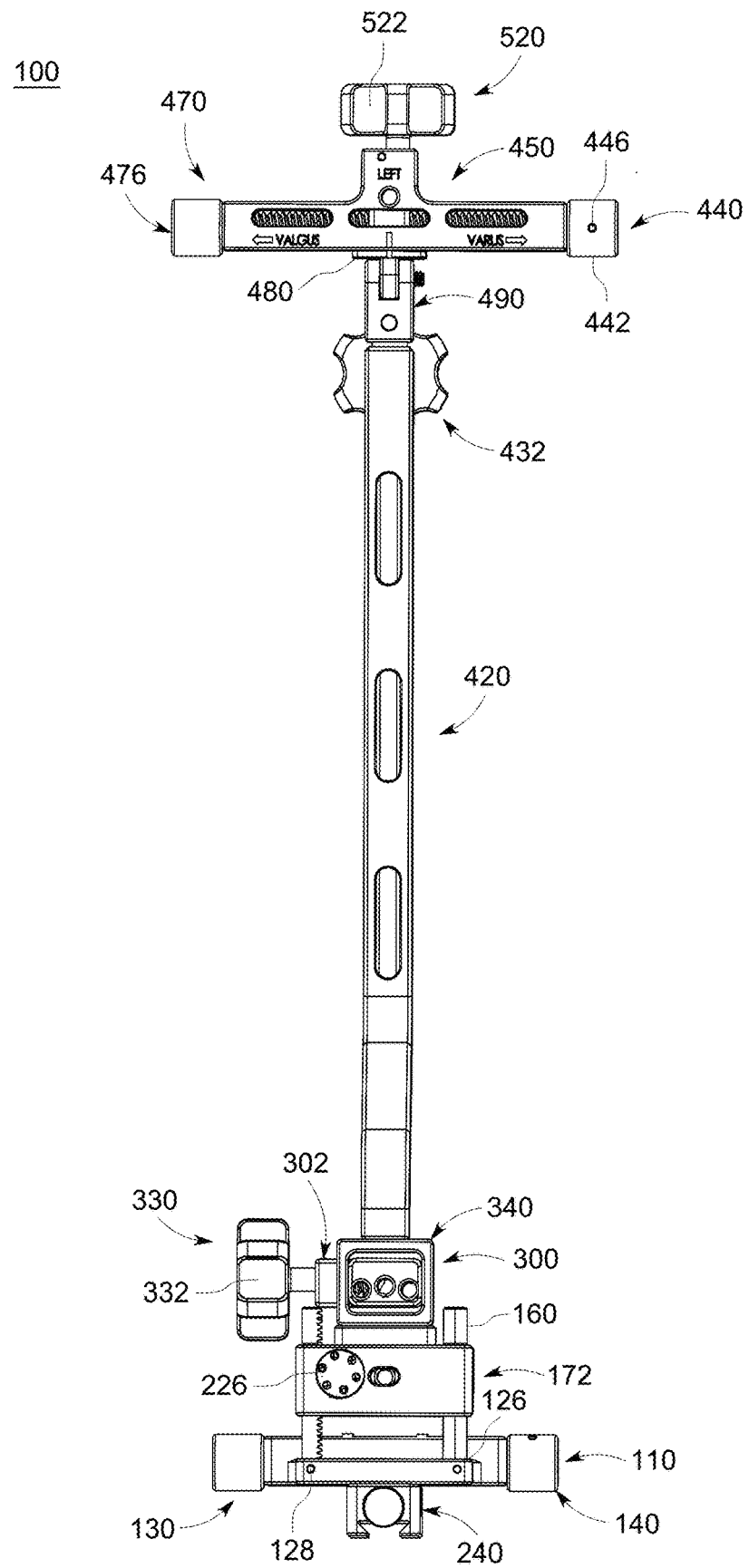
FIG. 4 is a second side view of the tibia alignment guide of FIG. 1, in accordance with an aspect of the present disclosure.
Figure 5:
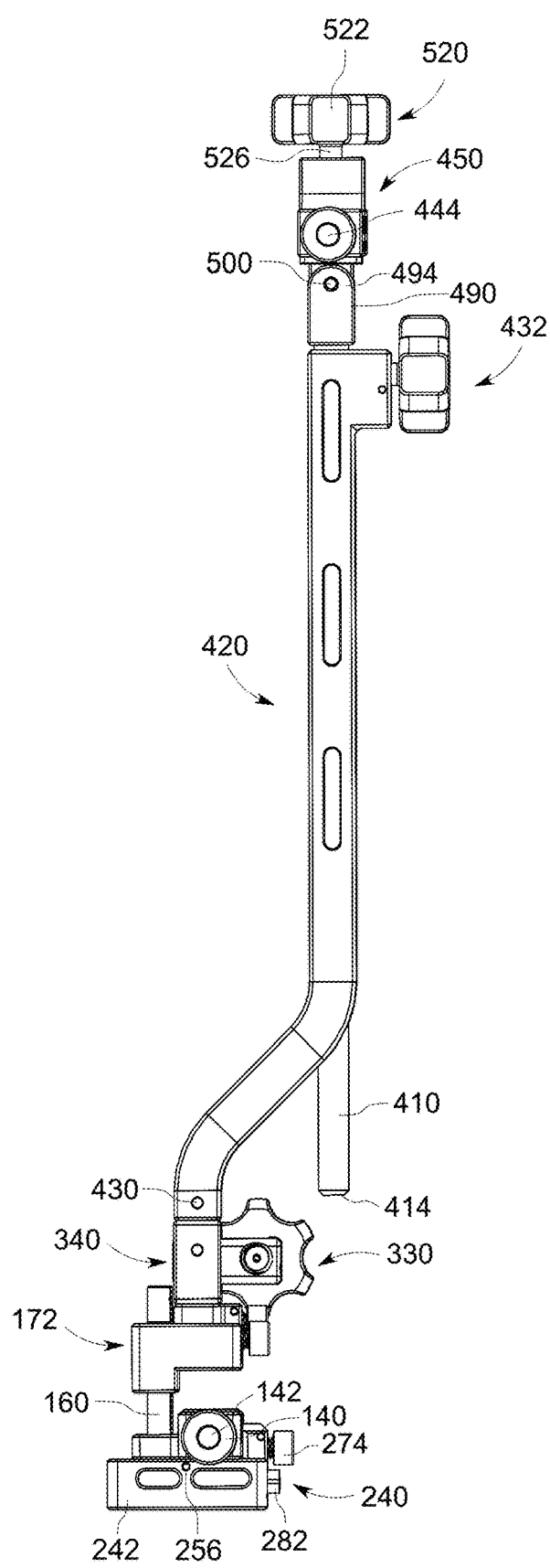
FIG. 5 is a first end view of the tibia alignment guide of FIG. 1, in accordance with an aspect of the present disclosure.
Figure 6:
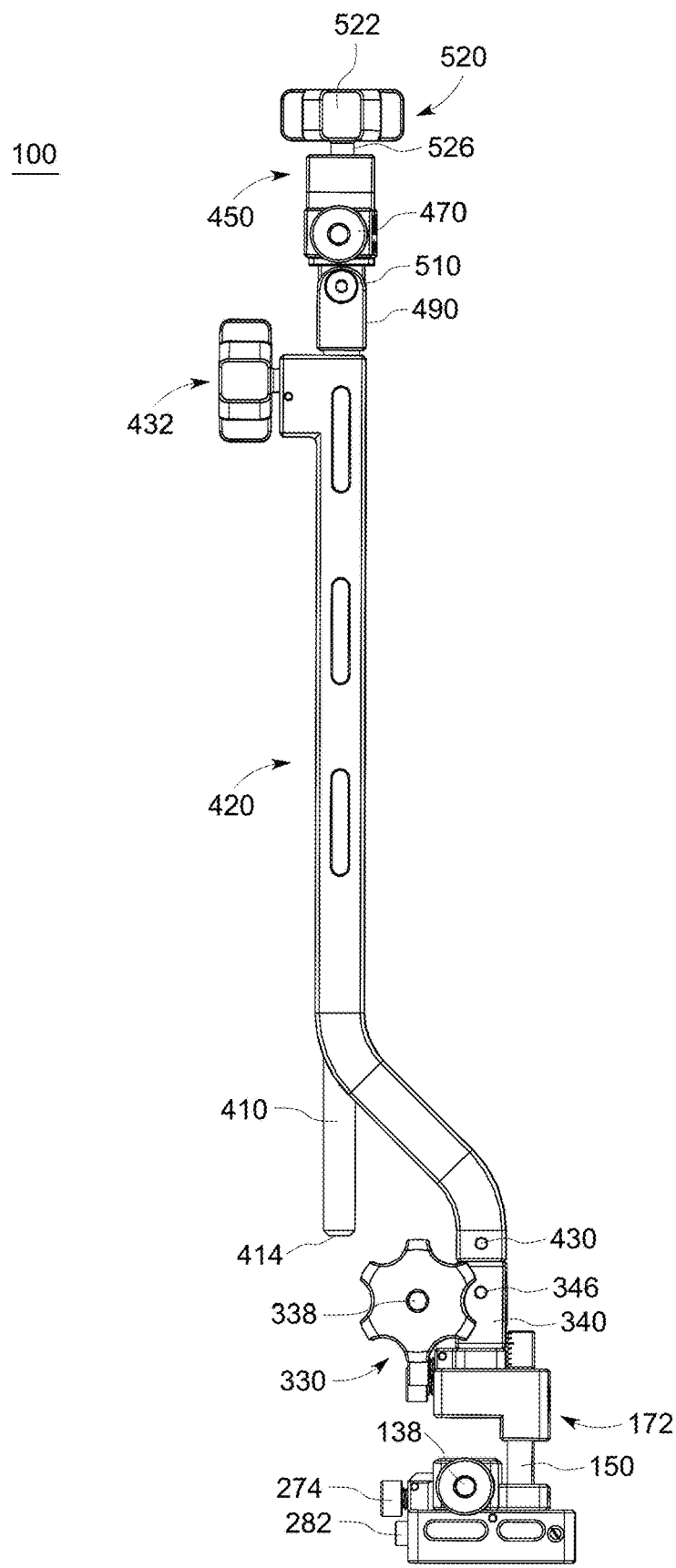
FIG. 6 is a second end view of the tibia alignment guide of FIG. 1, in accordance with an aspect of the present disclosure.
Figure 7:
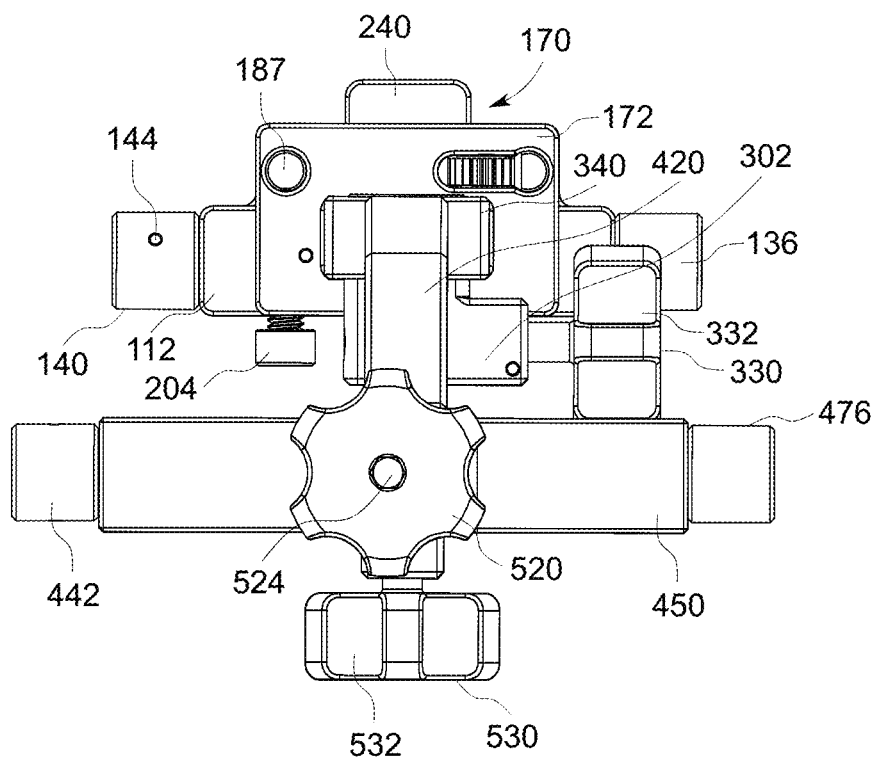
FIG. 7 is a superior view of the tibia alignment guide of FIG. 1, in accordance with an aspect of the present disclosure.
Figure 8:
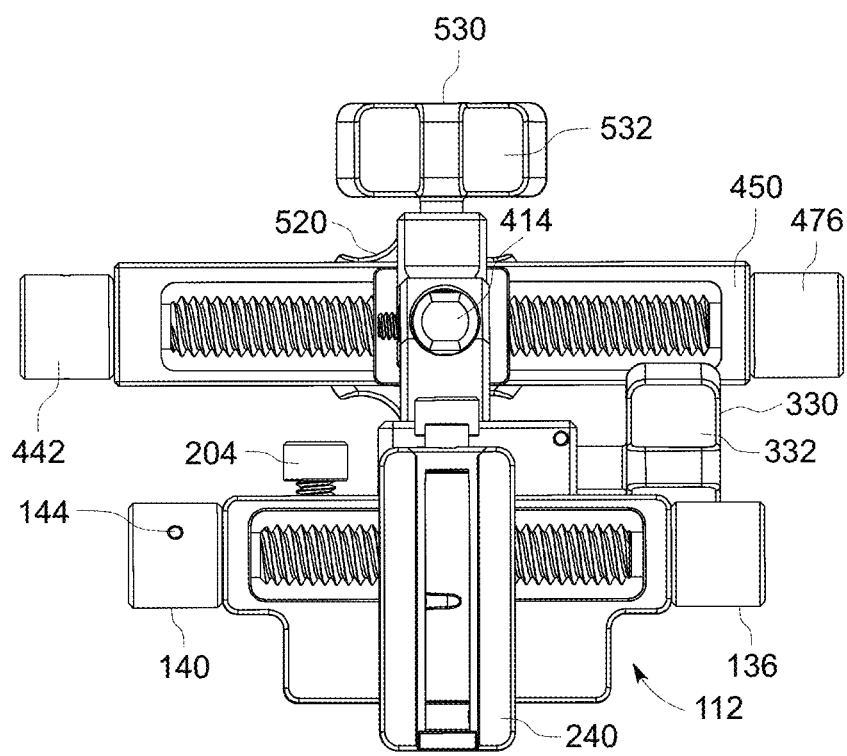
FIG. 8 is an inferior view of the tibia alignment guide of FIG. 1, in accordance with an aspect of the present disclosure.
Figure 10:
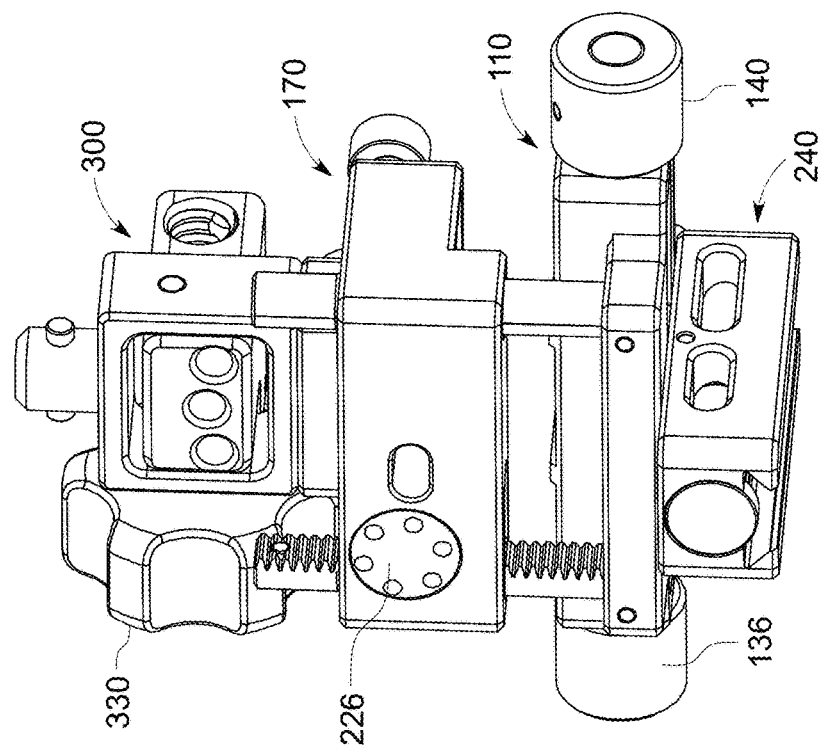
FIG. 10 is a second perspective view of the first translation mechanism, the second translation mechanism and the coupling member of FIG. 9, in accordance with an aspect of the present disclosure.
Figure 9:
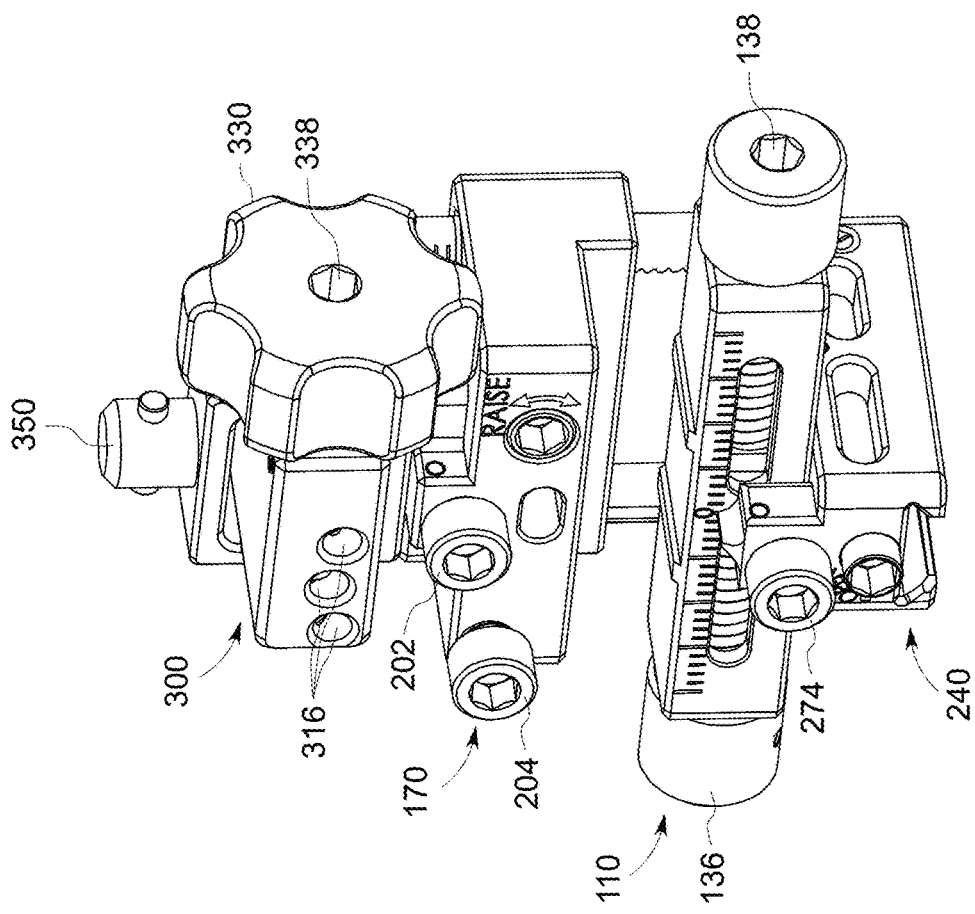
FIG. 9 is a first perspective view of a first translation mechanism, a second translation mechanism and a coupling member of the tibia alignment guide of FIG. 1, in accordance with an aspect of the present disclosure.
Figure 12:
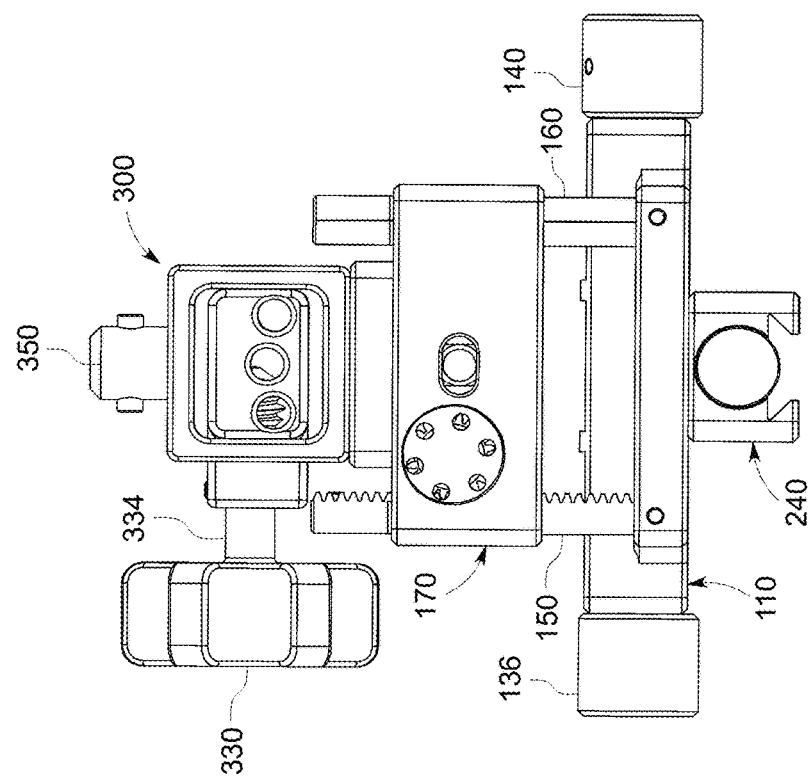
FIG. 12 is a second side view of the first translation mechanism, the second translation mechanism and the coupling member of FIG. 9, in accordance with an aspect of the present disclosure.
Figure 11:
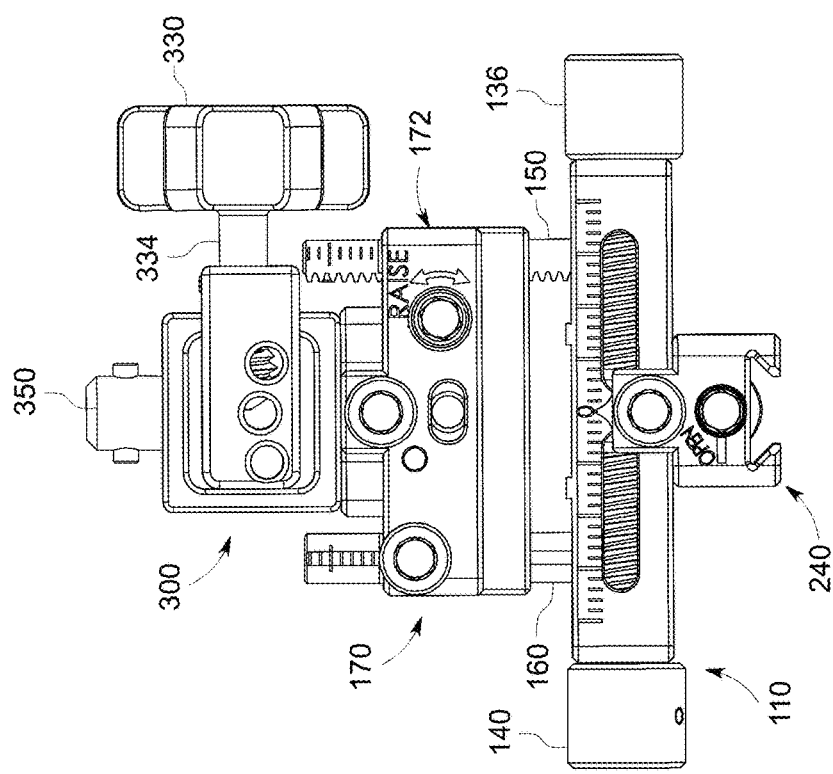
FIG. 11 is a first side view of the first translation mechanism, the second translation mechanism and the coupling member of FIG. 9, in accordance with an aspect of the present disclosure.
Figure 14:
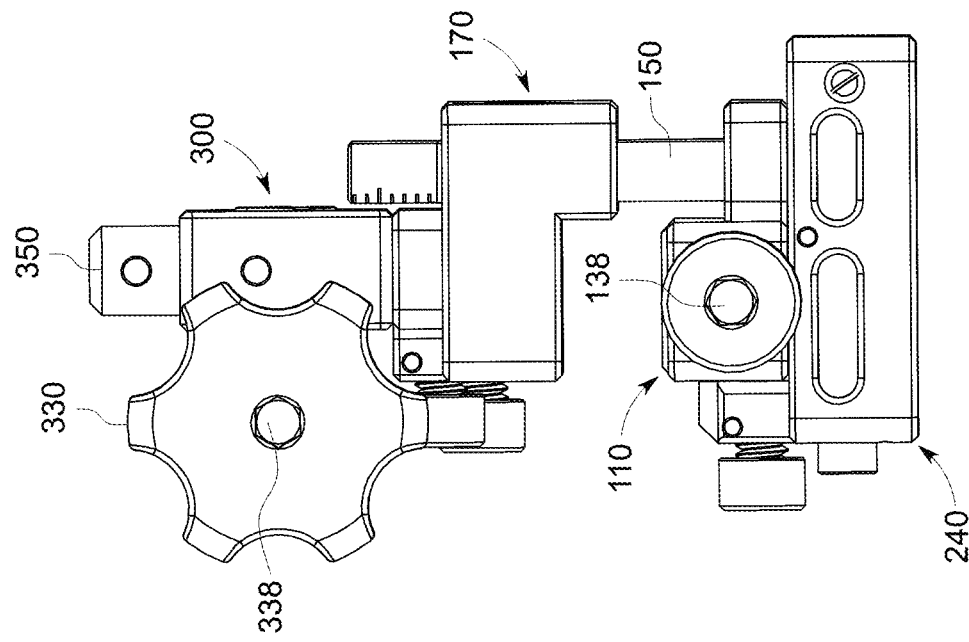
FIG. 14 is a second end view of the first translation mechanism, the second translation mechanism and the coupling member of FIG. 9, in accordance with an aspect of the present disclosure.
Figure 13:
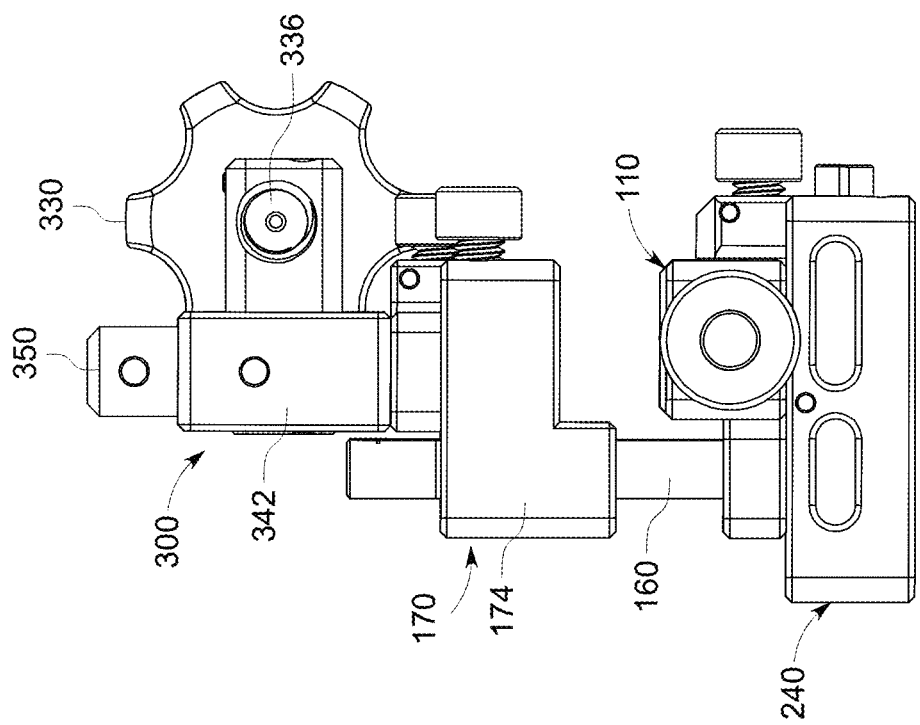
FIG. 13 is a first end view of the first translation mechanism, the second translation mechanism and the coupling member of FIG. 9, in accordance with an aspect of the present disclosure.

Referring now to FIGS. 15-20, the first translation mechanism 110 includes a housing 112, a fastening member, fastener, or screw 130 received within the housing 112, and a coupling member or cap 140 secured to the fastening member 130. The housing 112 may include a first opening 114 positioned at a first end and extending into the housing 112 and a second opening 116 positioned at a second end and extending into the housing 112. The first opening 114 may be aligned with the second opening 116 to receive the fastening member 130. The housing 112 may further include a cavity 118 extending into the housing 112 from a bottom or distal surface. The cavity 118 may intersect with the first opening 114 of the second opening 116. The cavity 118 may also receive a portion of the fastening member 130 when the first translation member 110 is assembled. In addition, the housing 112 may include at least one window 120 extending from a first side of the housing 112 into the cavity 118. In the depicted embodiment, the at least one window 120 is two windows 120, although alternative numbers of windows 120 are also contemplated and may include, for example, one or more windows 120. The housing 112 may also include a plurality of dimension markings 122 positioned along at least a portion of the first side of the housing 112. Further, the housing 112 includes a foot or extension member 124 extending away from a second side of the housing 112. The extension member 124 may be, for example, positioned near the distal end of the second side of the housing 112. As shown in FIG. 4, the extension member 124 may include a first recess 126 positioned at the first end of the housing 112 and a second recess 128 positioned at the second end of the housing 112.

With continued reference to FIGS. 15-20, the fastening member 130 may include a shaft portion 132 and a head portion 136. The head portion 136 may be coupled to a first end of the shaft portion 132. The head portion 136 may also include a drive opening 138 positioned on the first end of the head portion 136 opposite the shaft portion 132. The drive opening 138 may be, for example, sized and shaped or configured to receive a driving tool, such as a screw driver, to rotate the fastening member 130. The shaft portion 132 may be, for example, threaded along at least a portion of the shaft 132 and may include a locking opening 134. The locking opening 134 may be positioned, for example, perpendicular to a longitudinal axis of the fastening member 130. The locking opening 134 may be, for example, sized and shaped or configured to receive a pin or locking member 146. As shown in FIGS. 15-20, the shaft portion 132 is threaded from the head portion 136 toward the second end and includes a non-threaded section near the second end of the shaft portion 132. The coupling member 140 may include a through hole 142 extending from a first end to a second end. The coupling member 140 may also include a locking opening 144 extending from a side of the coupling member 140 into the through hole 142. The locking opening 144 may be, for example, generally perpendicular to the through hole 142. The locking opening 144 may receive a pin or locking member 146 to secure the coupling member 140 to the fastening member 130.

The alignment guide 100 may also include a first distal-proximal translating member 150 and a second distal-proximal translating member 160, as shown in at least FIGS. 15-20. The first translating member 150 may include a body 152 with a first opening or securement opening 154 positioned at a distal end of the body 152. The first opening 154 may extend through the body 152 from a first side to a second side. In addition, the first translating member 150 may include a groove 156 positioned around the body 152 between a midpoint of the body 152 and the proximal end of the body 152. The first translating member 150 may also include a plurality of teeth 158 extending along at least a portion of the length or in the direction of the longitudinal axis of the body 152 from the first end to the second end. The first translating member 150 may also include a plurality of dimension markings 159 positioned along at least a portion of the length or in the direction of the longitudinal axis of the body 152. The second translating member 160 may include a body 162 with a first opening or securement opening 164 positioned at a distal end of the body 152. In addition, the second translating member 160 may include a groove 166 positioned around the body 162 between a midpoint of the body 162 and the proximal end of the body 162. The second translating member 160 may also include a plurality of dimension markings 168 positioned along at least a portion of the length or in the direction of the longitudinal axis of the body 162.

With continued reference to FIGS. 15-20, the first translation mechanism 110 also includes the coupling member 240. The coupling member 240 includes a base 242, a securement fastener or telescoping rod knob 274 received within the coupling member 240, and a drive member 276 rotatably coupled to the base 242 of the coupling member 240. The base 242 may include a through hole 244 extending into the base 242 from a first side. The base 242 may also include a channel 246 extending into the base 242 from a bottom surface. The channel 246 may include a female dovetail portion or receiving member 248. The receiving member 248 may include a first protrusion 250 positioned on a first side of the bottom surface and a second protrusion 252 positioned on a second side of the bottom surface. The channel 246 may include an opening at the bottom surface that may be, for example, smaller than the width of the interior top surface of the channel 246. For example, the channel 246 may have angled side surfaces as the channel 246 extends into the base 242. In addition, the base 242 may include at least one window 254 extending from the first end into the channel 246 and at least one window 254 extending from the second end into the channel 246. The base 242 may also include a locking pin opening 256 extending from the first end to the second end, for example, between the two windows 254. The base 242 may further include an engagement pin opening 258 extending into the base 242 from the first end.

A locking member or indicator member 260 may extend away from a top surface of the base 242 on the first side, as shown in FIGS. 15-20. The locking member 260 may include a through hole 262 extending from the first side toward the second side of the base 242. In addition, the locking member 260 may include a pointer 264 extending away from a top surface of the locking member 260. The pointer 264 may have, for example, a generally triangular shape or alternative shape which terminates in a point. Finally, the locking member 260 may include a locking pin opening 266 extending between the first end and the second end and positioned near a top surface of the locking member 260. The locking pin opening 266 may extend through the locking member 260, for example, perpendicular or generally perpendicular to the through hole 262. A translating protrusion 270 may also extend away from a top surface of the base 242 adjacent to the locking member 260. The translating protrusion 270 may include a through hole or threaded hole 272 extending between the first end and the second end. The locking member 260 may be spaced apart from the translating protrusion 270 to form a channel and the channel may be, for example, sized and shaped or configured to receive a side of the housing 112.

The securement fastener 274 may include, for example, a head portion with a drive feature and a shaft portion extending away from a second end of the head portion. The shaft portion may be, for example, threaded along at least a portion of its length. The drive member 276 may include a shaft 278 and a first groove 280. The first groove 280 may be, for example, inset into the shaft 278 and may extend around at least a portion of the circumference of the shaft 278. The drive member 276 may also include a drive shaft 282 with a drive opening 284 at a first end of the drive member 276. The drive shaft 282 may have, for example, a diameter smaller than the diameter of the shaft 278. In addition, the head portion 286 may be coupled to the second end of the drive member 276 and there may be a second groove 288 positioned between shaft 278 and the head portion 286. The drive member 276 may further include a locking pin opening 290 extending through the drive member 276 and positioned within the second groove 288.

With continued reference to FIGS. 15-20, the second translation mechanism, distal-proximal adjustment member, or gearbox 170 may include a housing 172, a coupling fastener or internal-external adjustment screw 202, a locking fastener 204, a drive member 212, an engagement member 218, and a locking cap 226. The housing 172 may include a base 174 with a first extension member or proximal extension member 190 extending away from a top surface of the base 174 and a second extension member or distal extension member 200 extending away from a bottom surface of the base 174. The base 174 may also include a fastener hole 176 positioned near the second end of the housing 172 and a fastener hole or locking hole 192 extending at least partially through the first extension member 190 from a first side into a coupling hole or recess 196. The base 174 may also include a locking pin hole 178 positioned between the fastener hole 136 and the locking hole 192. The base 174 may further include a through hole or alignment pin hole 180 extending through the base 174 from a first side to a second side. The through hole 180 may have, for example, an oval or elliptical shape. The through hole 180 may be positioned below the fastener hole 192. The base 174 may also include a tool opening 182 positioned near the first end of the base 174. The locking cap opening 184 may extend into the base 174 from a second side and engage or overlap with the tool opening 182. The locking cap opening 184 may have, for example, a diameter larger than the diameter of the tool opening 182. The locking cap opening 184 may be, for example, threaded to receive a fastener 226. The housing 172 may also include the cavity 186 positioned within the base 174. The housing 172 may further include an enlarged opening or keyhole portion 188 extending through the base 174 and the distal extension member 200. The enlarged opening 188 may extend from the top surface of the base 174 into and through the cavity 186. In addition, the locking cap opening 184 may extend from a second side of the base 174 into the cavity 186.

Figure 15:
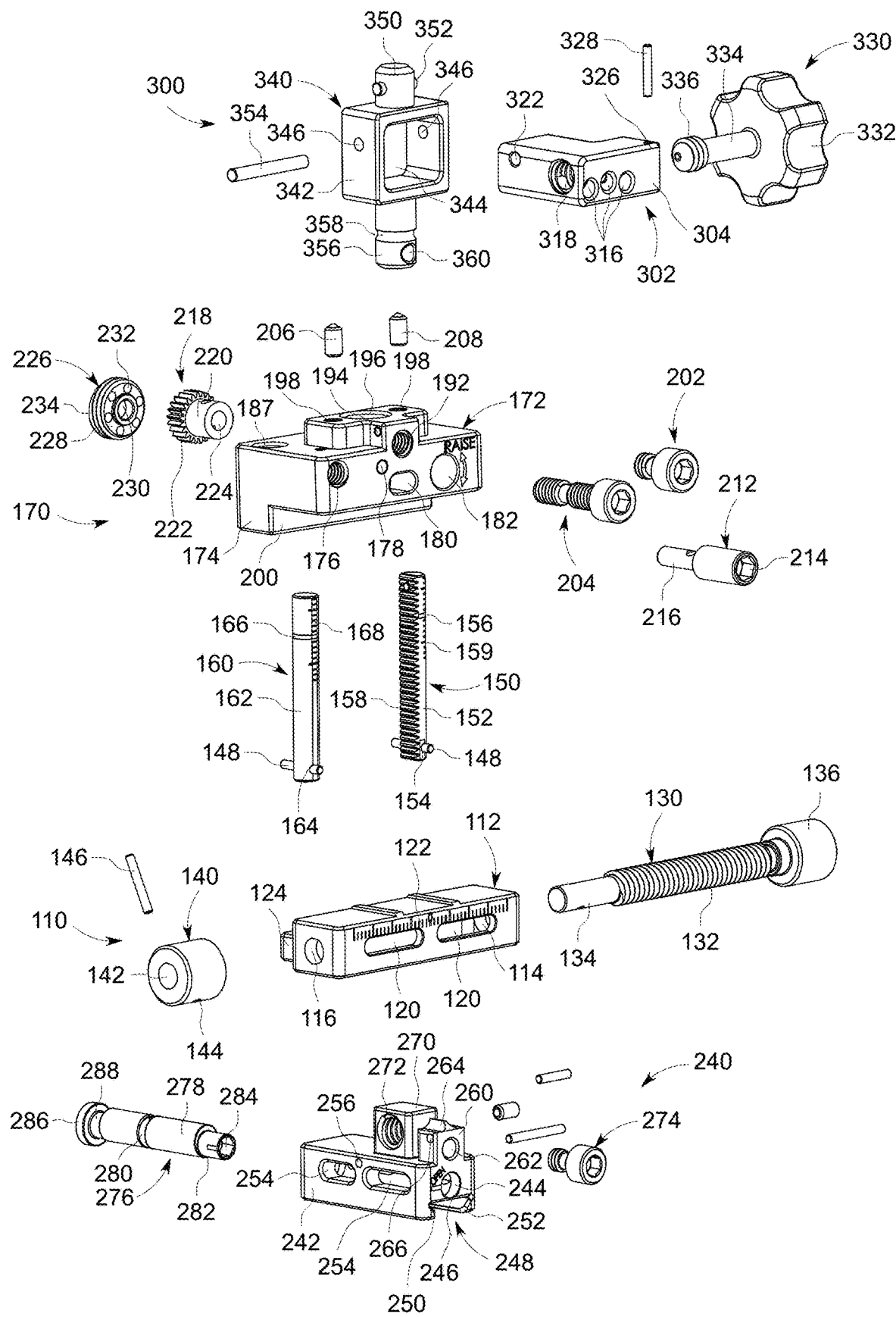
FIG. 15 is an exploded, first perspective view of the first translation mechanism, the second translation mechanism and the coupling member of FIG. 9, in accordance with an aspect of the present disclosure.
Figure 16:
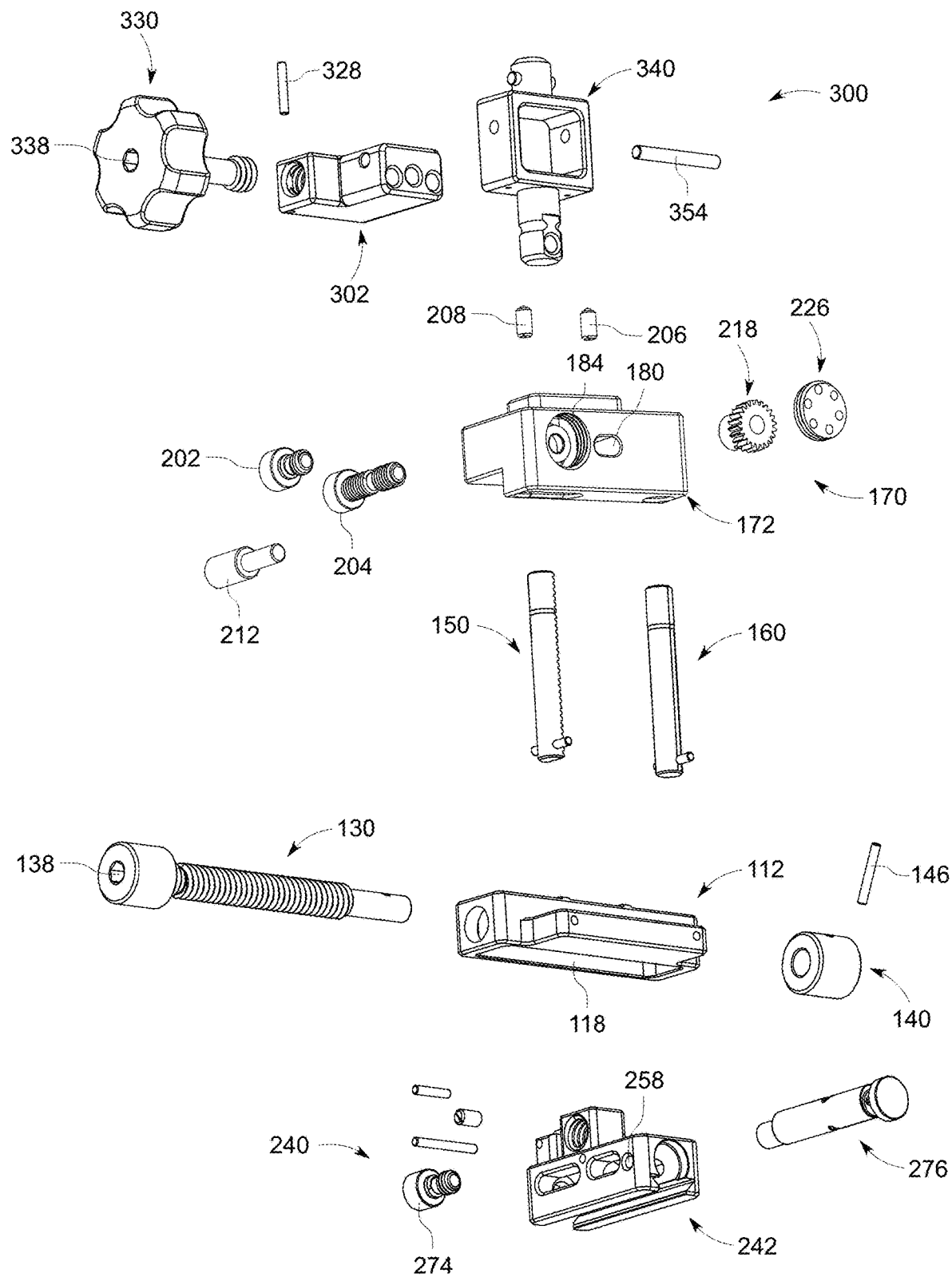
FIG. 16 is an exploded, second perspective view of the first translation mechanism, the second translation mechanism and the coupling member of FIG. 9, in accordance with an aspect of the present disclosure.
Figure 17:
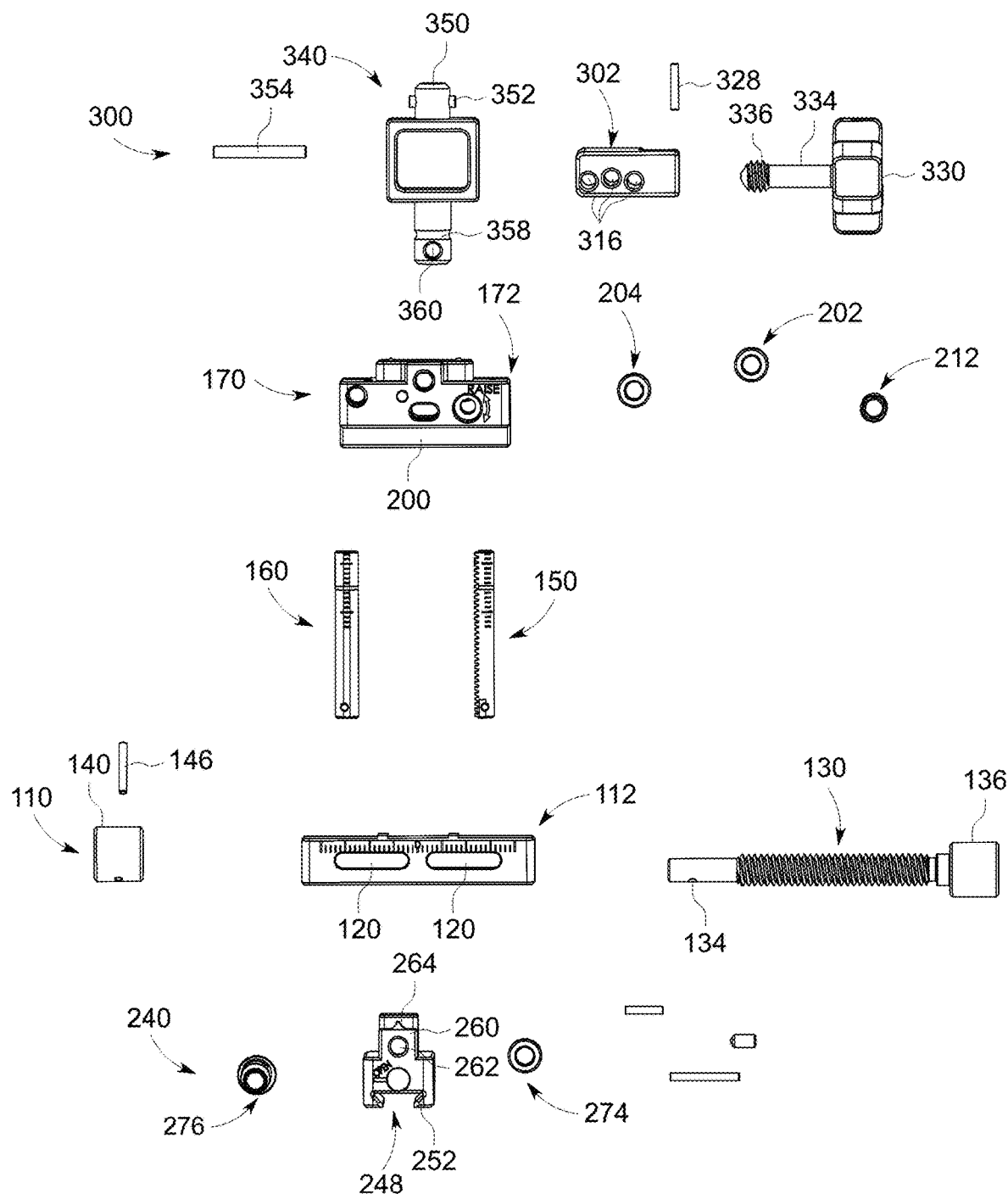
FIG. 17 is an exploded, first side view of the first translation mechanism, the second translation mechanism and the coupling member of FIG. 9, in accordance with an aspect of the present disclosure.
Figure 18:
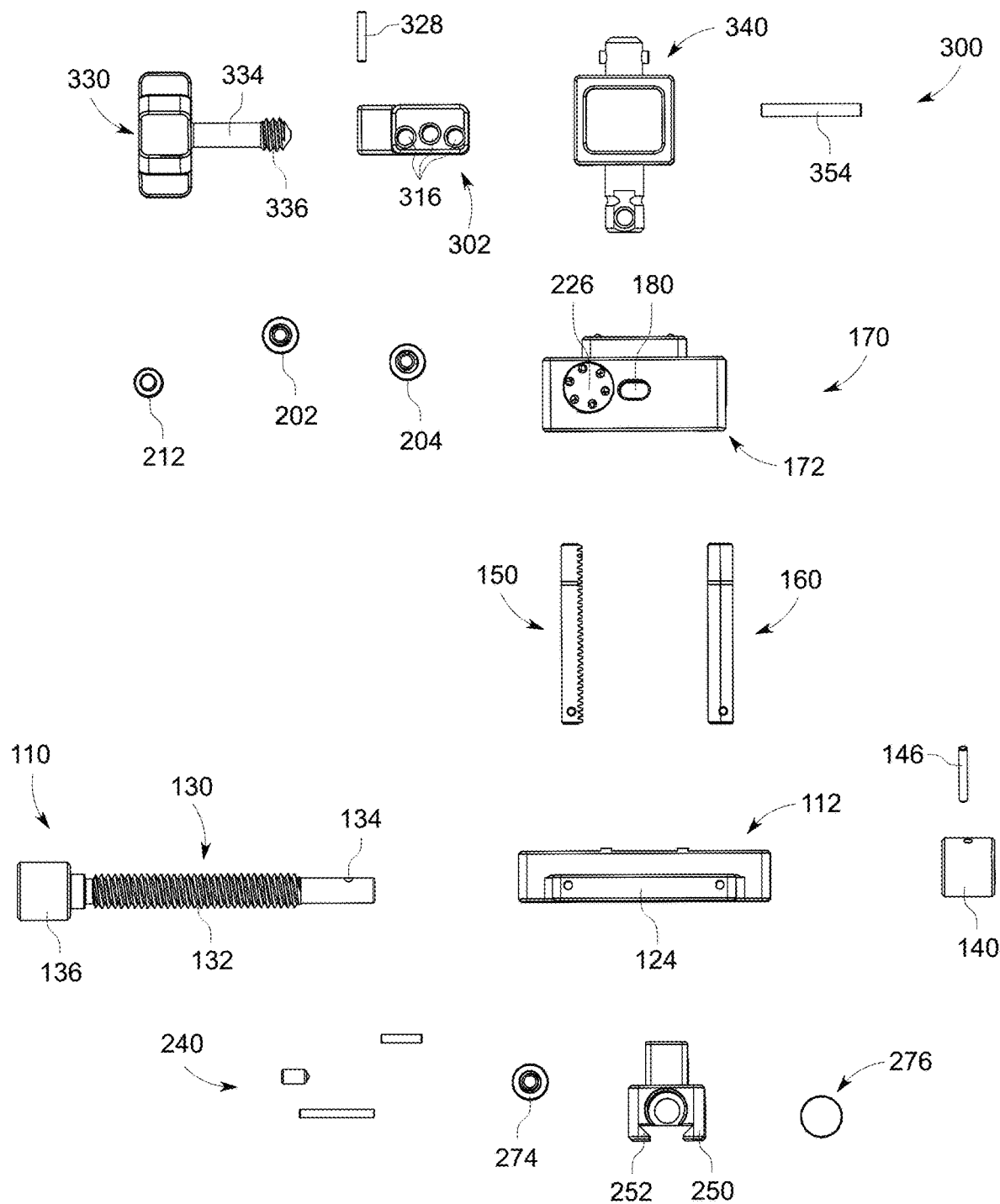
FIG. 18 is an exploded, second side view of the first translation mechanism, the second translation mechanism and the coupling member of FIG. 9, in accordance with an aspect of the present disclosure.
Figure 19:
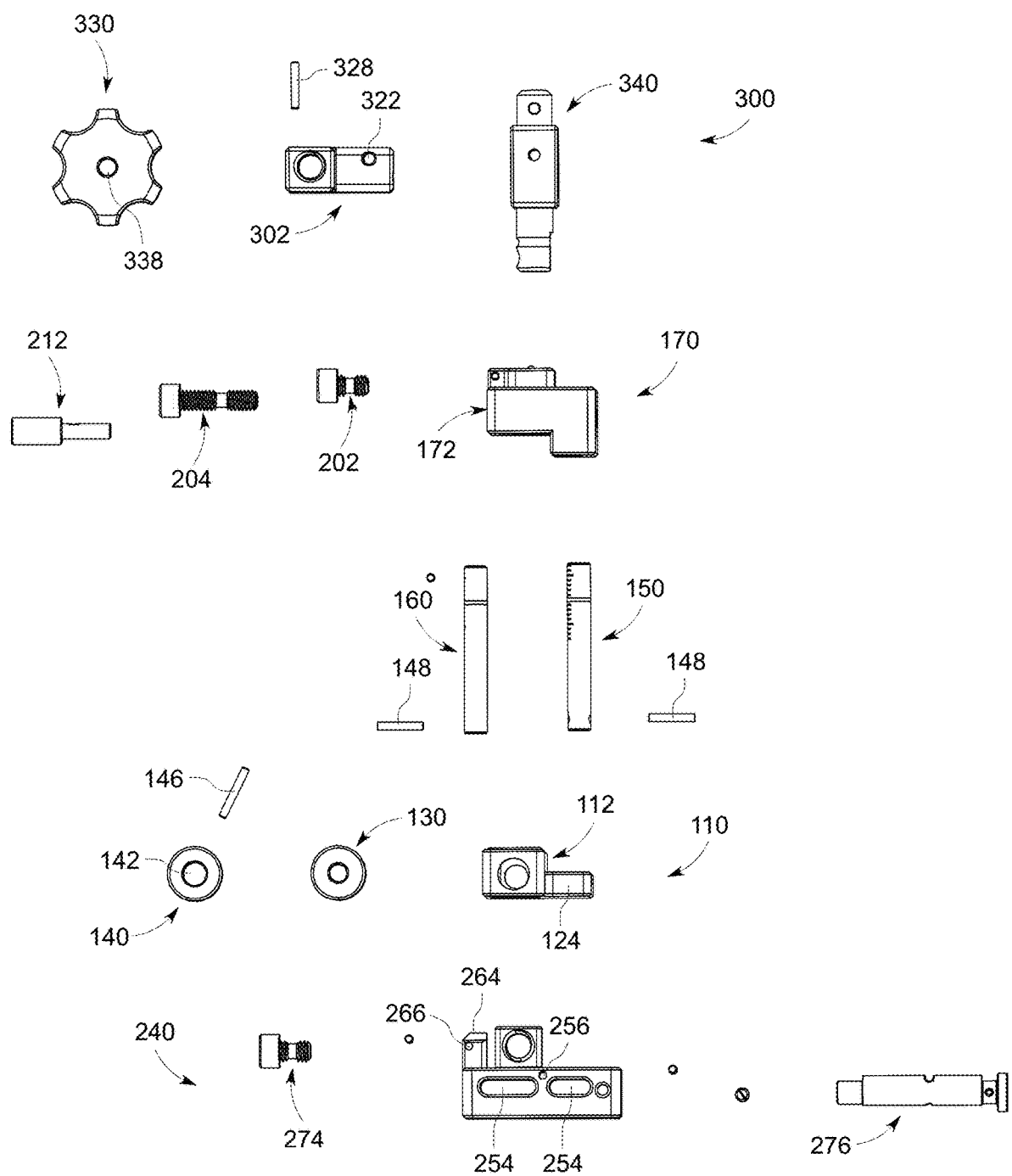
FIG. 19 is an exploded, first end view of the first translation mechanism, the second translation mechanism and the coupling member of FIG. 9, in accordance with an aspect of the present disclosure.
Figure 20:
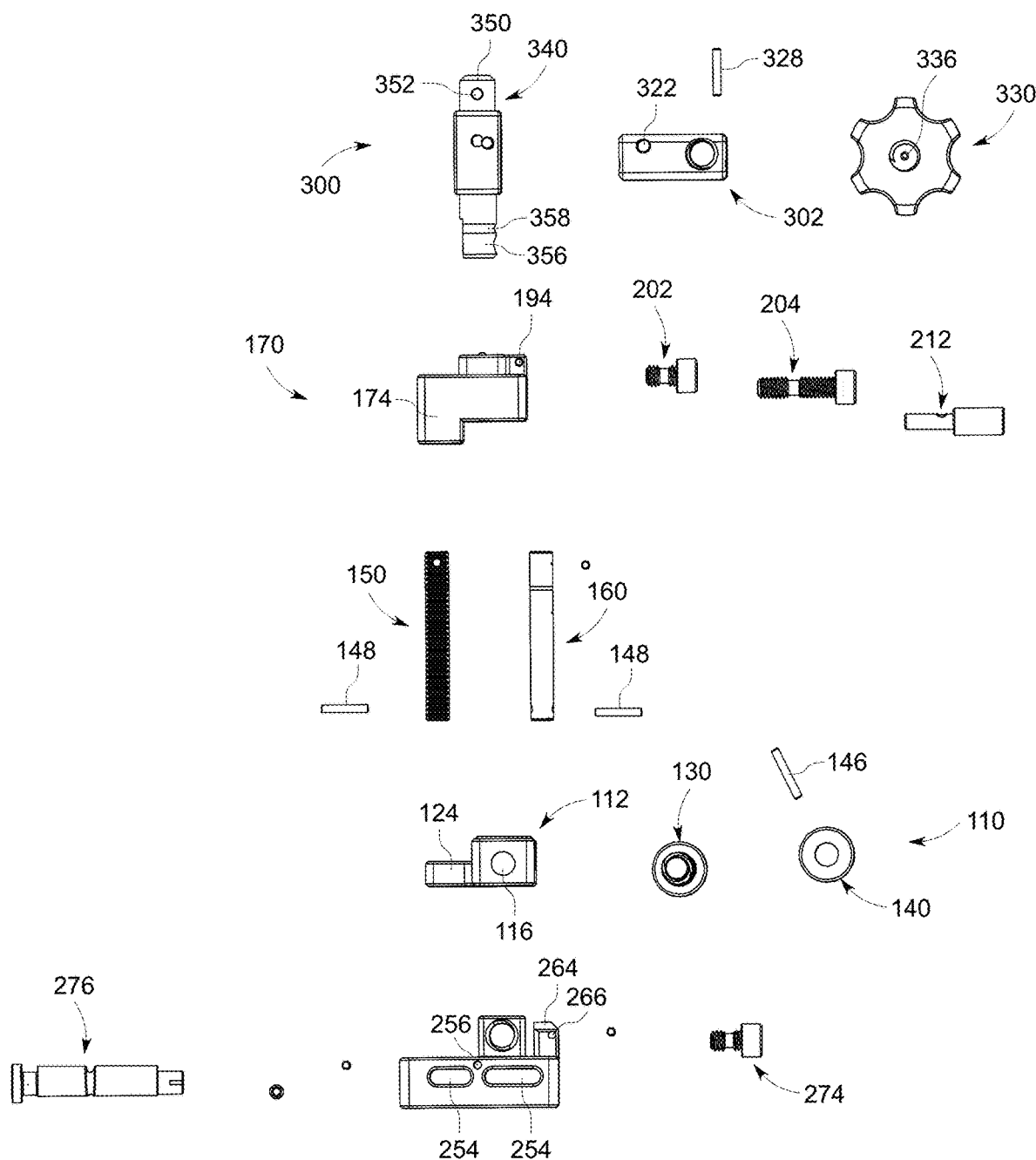
FIG. 20 is an exploded, second end view of the first translation mechanism, the second translation mechanism and the coupling member of FIG. 9, in accordance with an aspect of the present disclosure.
Figure 21:
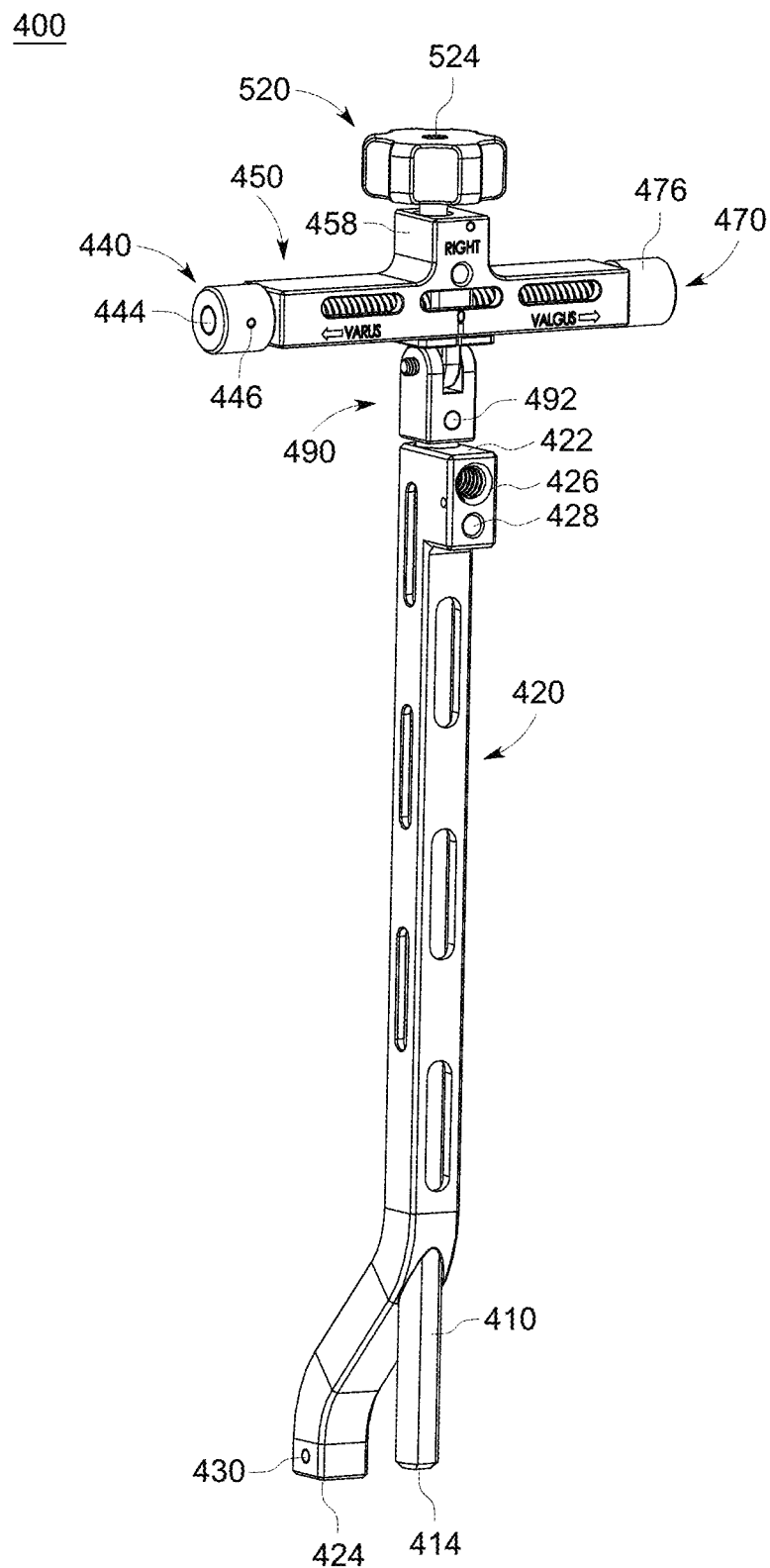
FIG. 21 is a first perspective view of a tower system of the tibia alignment guide of FIG. 1, in accordance with an aspect of the present disclosure.
Figure 22:
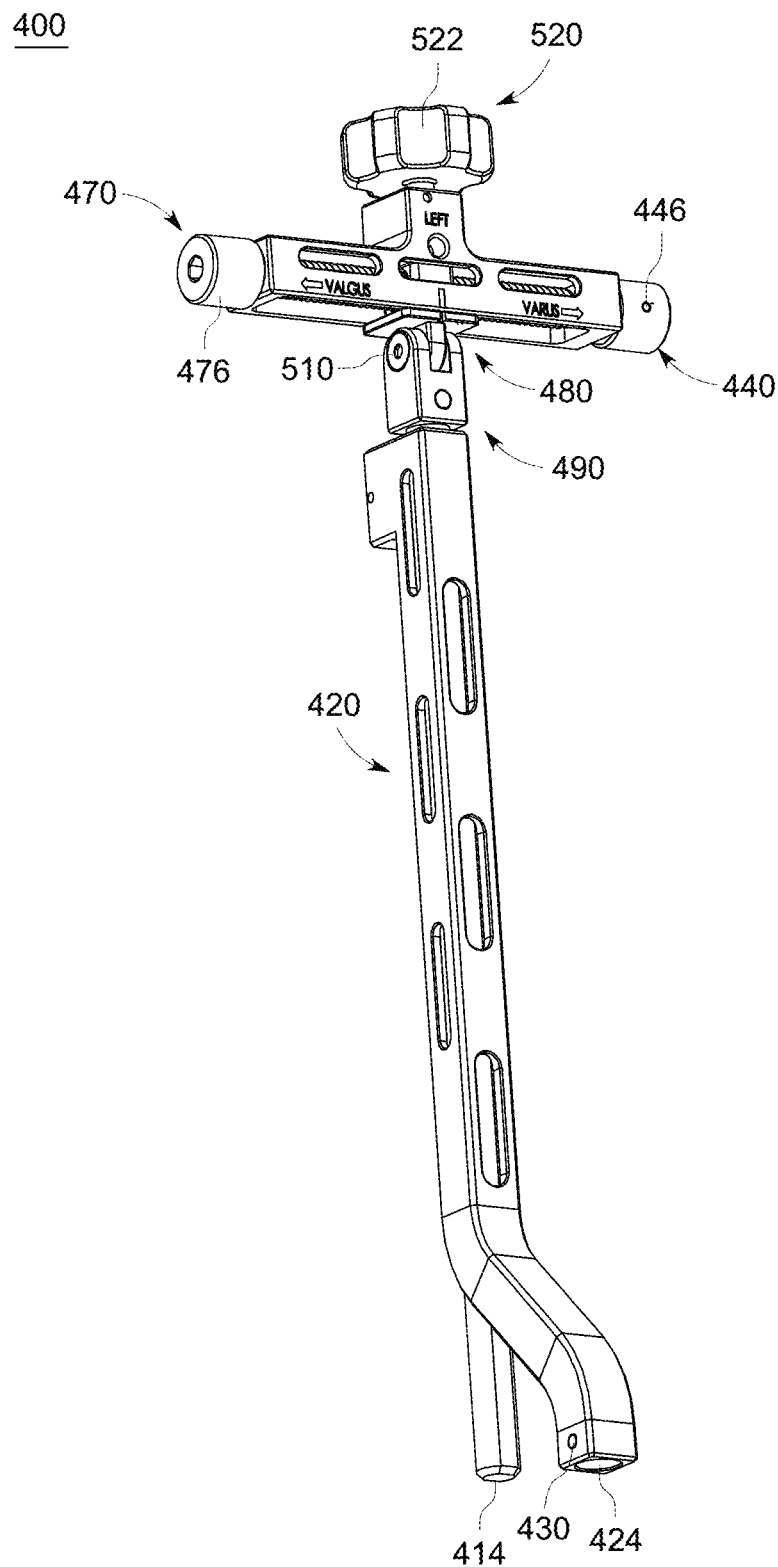
FIG. 22 is a second perspective view of the tower system of FIG. 21, in accordance with an aspect of the present disclosure.
Figure 23:
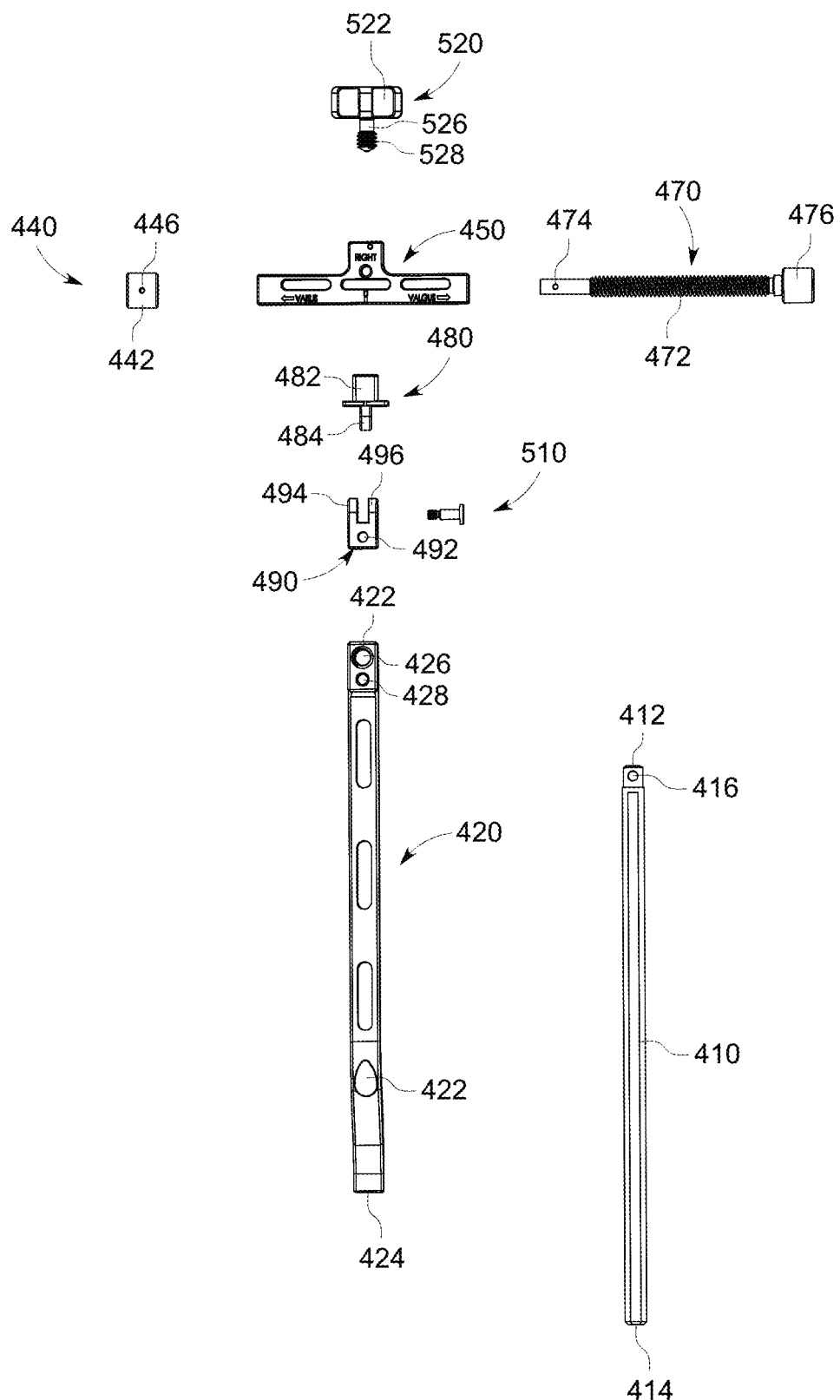
FIG. 23 is an exploded, first side view of the tower system of FIG. 21, in accordance with an aspect of the present disclosure.
Figure 24:
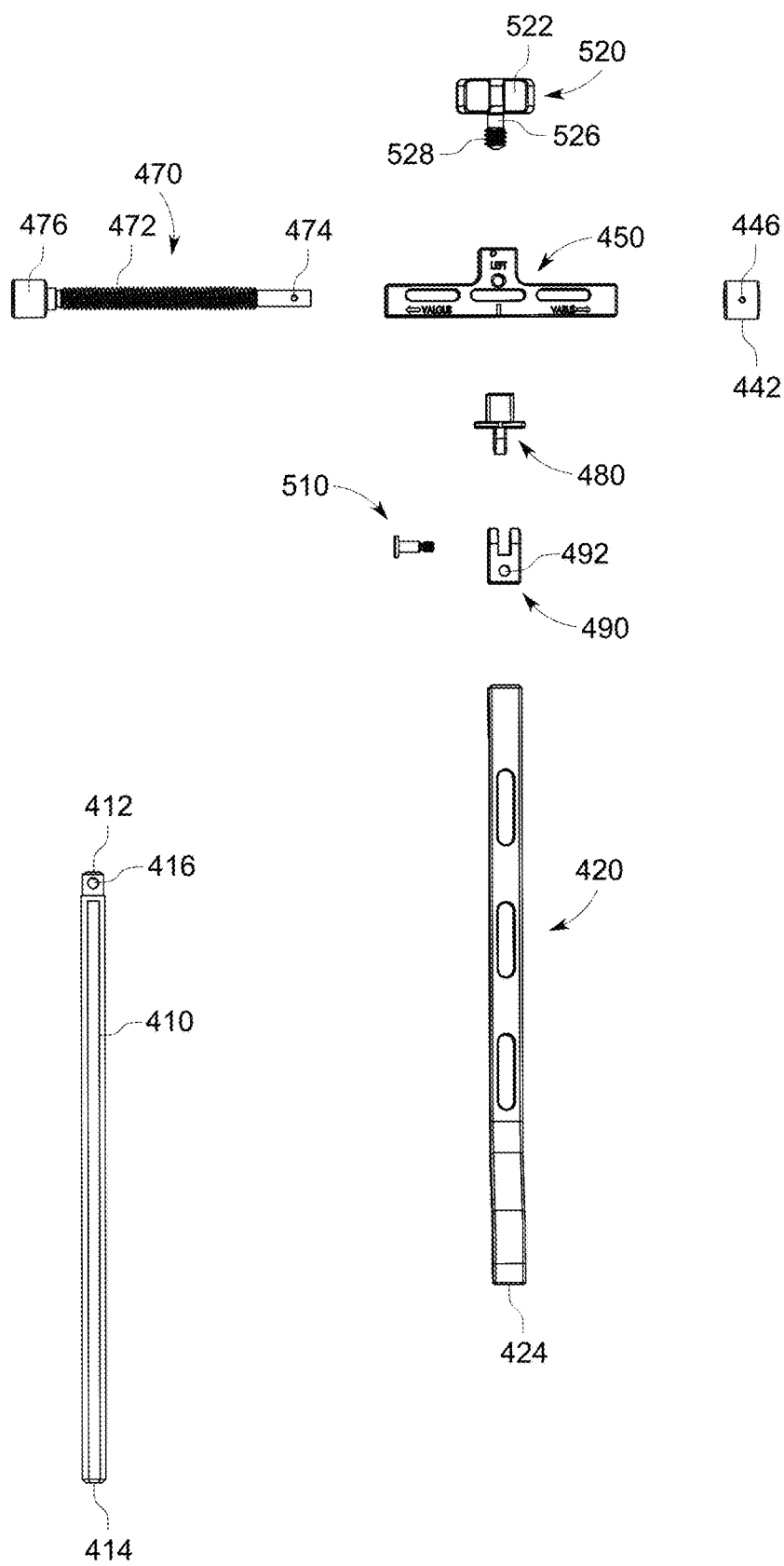
FIG. 24 is an exploded, second side view of the tower system of FIG. 21, in accordance with an aspect of the present disclosure.
Figure 25:
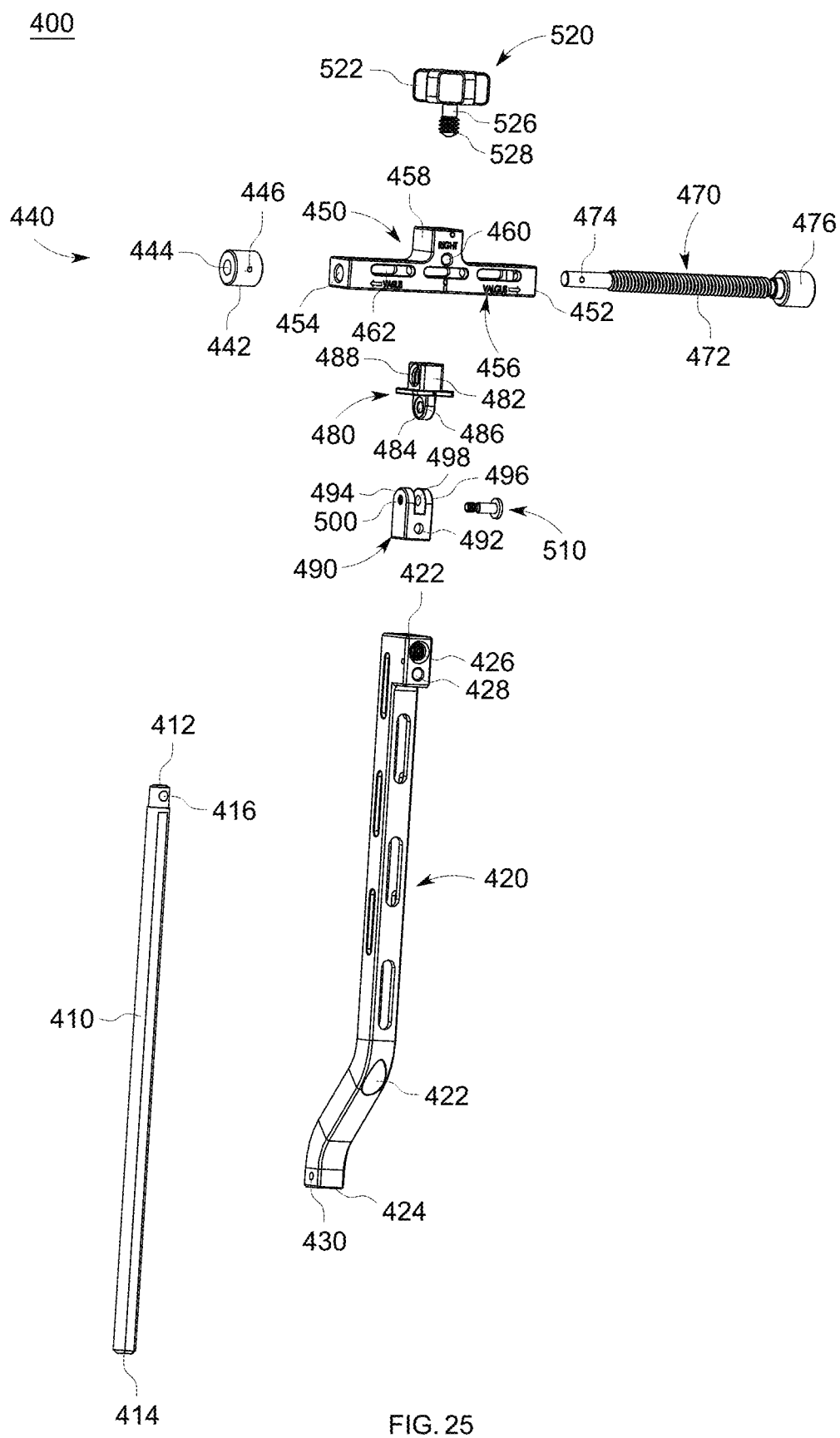
FIG. 25 is an exploded, first perspective view of the tower system of FIG. 21, in accordance with an aspect of the present disclosure.
Figure 26:
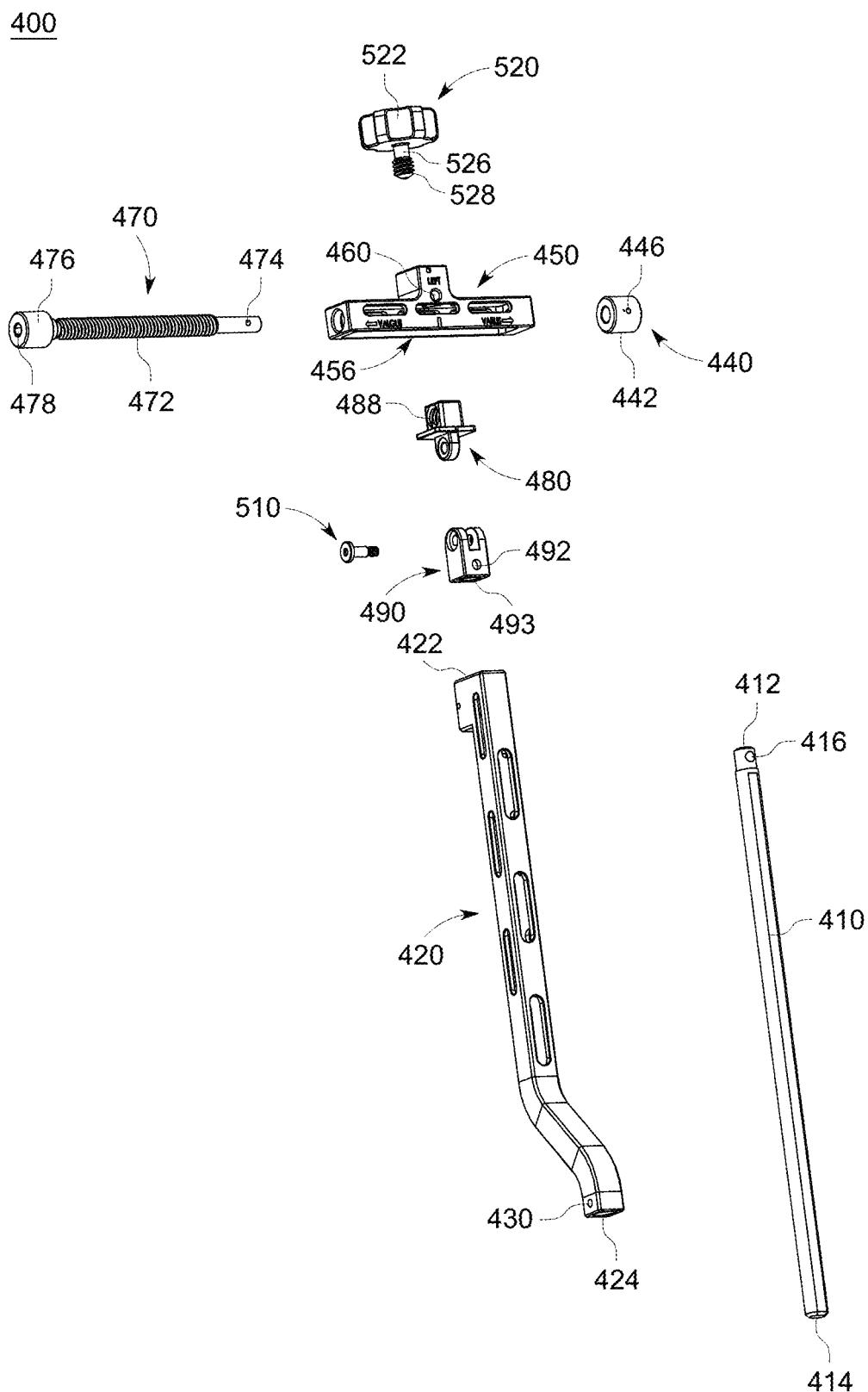
FIG. 26 is an exploded, second perspective view of the tower system of FIG. 21, in accordance with an aspect of the present disclosure.

As shown in at least FIGS. 15, 19 and 20, the housing 172 may also include a locking pin hole 194 extending through the first extension member 190 in a medial-lateral direction from the first end toward the second end. The first extension member 190 may also include the coupling hole 196 extending into the first extension member 190 from a superior or top surface. The coupling hole 196 may be, for example, a circular or a round recess or alternatively shaped recess corresponding to the shape of the stem 410 of the tower system 400. In addition, the first extension member 190 may also include two threaded recesses 198 positioned on opposite sides of the coupling hole 196. The threaded recesses 198 may be configured or sized and shaped to receive a first alignment pin 206 and a second alignment pin 208. The alignment pins 206, 208 when inserted may have a portion of the pins 206, 208 extending above the superior or top surface of the first extension member 190 to engage a bottom surface of the housing 340 of the coupling member 300. The second extension member or distal extension member 200 may extend away from an inferior or bottoms surface, as well as between the first end and the second end of the base member 174. In addition, the cavity 186 may extend through the base 174 as well as the second extension member 200 from a top surface to a bottom surface of the housing 172. The cavity 186 may be positioned near a first end of the housing 172. The housing 172 may also include a through hole 187 positioned near a second end of the housing 172. The through hole 187 may extend through the base 174 as well as the second extension member 200 from the top surface to the bottom surface of the housing 172. The cavity 186 and the through hole 187 may be, for example, configured or sized and shaped to receive the first translating member 150 and the second translating member 160, respectively.

The second translation mechanism 170 may also include a coupling fastener or internal external adjustment screw 202 for engagement with the fastener hole 192 of the housing 172, as shown in at least FIGS. 15-20. In addition, the second translation mechanism 170 may include a locking fastener 204 received within the fastener hole 176. The fastener hole 176 extends into the through hole 187 to enable the locking fastener 204 to engage the second translating member 160 and secure the second translating member 160 at a desired height. The second translation mechanism 170 may also include a drive member 212 with a first portion including a drive opening 214 at a first end and a driveshaft 216 extending away from the first portion to the second end. The driveshaft 216 may engage or be received within a through hole 224 of an engagement member 218. The engagement member 218 may also include a body or shaft 220 and a plurality of teeth 222 extending around the circumference of the exterior surface of the body 220. The plurality of teeth 222 may extend along only a portion of the length of the body 220 between a first end and second end of the engagement member 218. The plurality of teeth 222 may be, for example, configured or sized and shaped to engage the plurality of teeth 158 of the first translating member 150. The through hole 224 may extend through the body 220 along the entire length of the engagement member 218. The driveshaft 216 may extend completely through the through hole 224 to engage the locking cap 226. Although not shown, a washer may be positioned between the engagement member 218 and the locking cap 226 when assembled with the drive member 212. The locking cap 226 may include a body 228 and a through hole 230 extending through the body 228 from the first end to a second end. The locking cap 226 may also include recesses or drive features 232 inset into the first end and the second end of the body 228. Further, the locking cap 226 may include threads 234 along the exterior circumference between the first end and the second end of the body 228. The threads 234 may be, for example, configured or sized and shaped to engage the locking cap opening 184.

With continued reference to FIGS. 15-20, the coupling member 300 may include a housing 340, an alignment pin housing 302, and a securement knob 330. The alignment pin housing 302 is received within a through hole 344 of the housing 340 and secured together with a locking pin 354. In addition, the securement knob 330 is received within a through hole or threaded hole 318 of the alignment pin housing 302 to secure the coupling member 300 to a pin, for example, a pin 108. The housing 340 may include a base 342 with a through hole 344. The base 342 may have, for example, a generally square or rectangular shape, although other shapes are also contemplated. The base 342 may also include a through hole 346 extending through the two sides of the base 342 for receiving a pin 354 to couple the alignment pin housing 302 to the base 342. The housing 340 may also include a stem 356 extending away from an inferior or bottom surface of the base 342. The stem 356 may include a groove 358 extending around at least a portion of the circumference of the stem 356. The stem 356 may also include a through hole 360 extending through the stem 356. The through hole 360 may be, for example, configured or sized and shaped to receive a fastener 202 to secure the housing 340 to the housing 172. The housing 340 may further include a proximal coupling protrusion 350 extending away from a superior or top surface of the base 342. The coupling protrusion 350 may include, for example, tabs 352 extending away from the exterior, side surface of the coupling protrusion 350 or a pin 352 extending through the coupling protrusion 350 to assist with engagement of the coupling member with the tower portion 400.

With continued reference to FIGS. 15-20, the alignment pin housing 302 includes a base 304, which may be, for example, "L" shaped. The housing 302 may also include at least one pin hole 316 extending into the base 304 from a first side to a second side. As shown, the at least one pin hole 316 may be, for example, three pin holes 316 positioned adjacent to each other in a generally linear arrangement. The housing 302 may also include a through hole 318 extending through the base 304 from a first end to a second end. The through hole 318 may be, for example, positioned perpendicular to the at least one pin hole 316. In addition, the housing 302 may include pin holes 322, 326 for receiving locking pins, such as, pin 328 to secure the securement knob 330 and pins (not shown) to the housing 302. The pin hole 322 may extend through the base 304 from a first end to a second end near a posterior surface. The pin hole 326 may extend through the base 304 from a superior surface to an inferior surface and positioned near the second end and the anterior surface.

In addition, the securement knob 330 includes a head or drive portion 332 and a stem or shaft 334 extending away from a bottom surface of the head portion 332. The shaft 334 may include a threaded portion 336 extending along at least a portion of the length of the shaft 334. The threaded portion 336 may be, for example, configured or sized and shaped to be inserted into the through hole 318. The securement knob 330 may also include a drive feature 338 inset into the first end of the head 332 of the knob 330.

Referring now to FIGS. 21-26, the tower 400 may include a coupling rod 410, which may be received within a tower base 420 to couple the second translation mechanism 170 to the third translation mechanism or varus-valgus adjustment member 440. The rod 410 may include a first end 412 and a second end 414. The first end 412 includes an opening 416 for coupling to the third adjustment member 440. The tower base 420 may couple to the coupling member 300 on a distal end. The tower base 420 may include a coupling opening 424 for receiving the proximal coupling protrusion 350 and a securement pin opening 430 on a first end for receiving the tabs 352 of the coupling member 300. The second end of the tower base 420 may include a securement protrusion with an opening 422 extending into the base 420 along the longitudinal axis of the base 420. The second end may also include a first or threaded opening 426 and a second opening 428 for coupling the tower base 420 to the third translation mechanism 440. The threaded opening 426 may be, for example, sized and shaped or configured to receive a knob 432. The knob 432 may be, for example, the same or similar to knob 520.

The third translation mechanism 440 may include a housing 450 with a first opening 452 at a first end, a second opening 454 at a second end and a cavity 456 extending into the housing 450 from a bottom surface and engaging or overlapping the through hole created by the first and second openings 452, 454. The third translation mechanism 440 may also include a fastening member 470, a cap 442, and a knob 520. The fastening member 470, which may be the same or similar to fastening member 130, which will not be described again here, in detail, for brevity sake. The fastening member 470 may include a shaft portion 472 and a head portion 476, which may be the same or similar to the shaft portion 132 and the head portion 136 of the fastening member 130. The head portion 476 may include a drive opening 478, which may be the same or similar to the drive opening 138. The shaft portion 472 may include a locking opening 474, which may be the same or similar to the locking opening 134. The coupling member 442 may be the same or similar to the coupling member 140. The coupling member 442 may include a through hole 444 and a locking opening 446, which may be the same or similar to the through hole 142 and locking opening 144. The locking opening 446 may receive a pin or locking member, such as the pin or locking member 146, to secure the coupling member 442 to the fastening member 470.

The fastening member 470 may be inserted through the first opening 452, cavity 456, and second opening 454 and extend at least partially beyond the second end. The portion of the fastening member 470 extending out of the second end of the housing 450 may couple to the cap 442. The third translation mechanism 440 may be coupled to the base 420 by a hinge member 480, 490. The first hinge member 480 may include a base 482 with an opening 488 extending through the base 482 from a first end to a second end. The opening 488 may be, for example, sized and shaped or configured to receive a portion of the fastening member 470. The first hinge member 480 may also include a coupling protrusion 484 with a through hole 486 extending through the coupling protrusion 484 from a first end to a second end. The second hinge member 490 may include a first arm member 494 and a second arm member 496 extending toward a superior end of the second hinge member 490. The first arm member 494 is spaced apart from and parallel to the second arm member 496 forming a channel 498 between the arm members 494, 496. The channel 498 may receive the coupling protrusion 484 of the first hinge member 480 of the third translation mechanism 440. A fastener 510 may be inserted through the first arm member 494, the coupling protrusion 484, and the second arm member 496 to rotatably couple the first hinge member 480 to the second hinge member 490.

The third translation mechanism 440 may allow the user to adjust the varus-valgus alignment as it rotates about the hinge members 480, 490. The third translation mechanism 440 may also include a proximal protrusion 458 extending away from a superior or top surface of the housing 450. The proximal protrusion 458 includes an opening extending into the protrusion 458 from the superior surface. The opening may receive a locking knob 520.

As shown in FIGS. 23-26, the locking knob 520 may include a head or drive portion 522 and a stem or shaft 526 extending away from a bottom surface of the head portion 522. The shaft 526 may include a threaded portion 528 extending along at least a portion of the length of the shaft 526. The threaded portion 528 may be, for example, configured or sized and shaped to be inserted into the opening in the proximal protrusion 458. The locking knob 520 may also include a drive feature 524 inset into the first end of the head 522 of the knob 520.

The first translation mechanism 110 may be assembled by, for example, inserting the translating protrusion 270 into the channel 246 of the base 242. The securement fastener 274 may be inserted through, for example, the through hole 262 to engage the first side of the housing 112. In addition, the drive member 276 may be inserted into the through hole 244 and an engagement pin (not shown) may be inserted through the engagement pin hole 258 until the engagement pin engages the groove 288 in the drive member 276. Then, the fastening member 130 may be inserted into the first opening 114, through the cavity 118 and the through hole 272 of the translating protrusion 270, and a portion of the fastening member 130 may extend out of the second opening 116. The through hole 142 of the coupling member 140 may receive the portion of the fastening member 130 extending out of the second opening 116. In addition, a pin 146 may be inserted into the locking opening 144 of the coupling member 140 and through the locking opening 134 of the fastening member 130 to retain the threaded portion of the shaft portion 132 within the cavity 118 of the housing 112.

Next, a distal end of the first translating member 150 may be inserted into the first recess 126 and a locking pin or locking member 148 may be inserted through the extension member 124 and the first opening 154 to secure the first translating member 150 to the extension member 124 of the housing 112. The distal end of the second translating member 160 may be inserted into the second recess 128 and a locking pin 148 may be inserted through the extension member 124 and second opening 164 to secure the second translating member 160 to the extension member 124 of the housing 112. Then, the second translation mechanism 170 may be aligned with and slid onto the translating members 150, 160. The first translating member 150 may be received within the cavity 186 of the housing 172 and a plurality of teeth 158 may engage the plurality of teeth 222 of the engagement member 218 to allow for the housing 172 to translate with respect to the coupled first translation mechanism 110 and coupling member 240. The engagement member 218 will be positioned within the cavity 186. The drive member 212 will be coupled to the engagement member 218 to allow for rotation of the drive member 212 from a first side to be translated to rotation of the engagement member 218. The locking cap 226 may also be inserted into the locking cap opening 184 to engage the second end of the drive member 212 and retain the engagement member 218 within the cavity 186. Further, the second translating member 160 may be inserted into the through hole 187 when the locking fastener 204 is positioned in an unlocked or first position. In use the locking fastener 204 may be moved to secure the second translating member 160 when the desired proximal distal position is achieved in a locked or second position.

Figure 27:
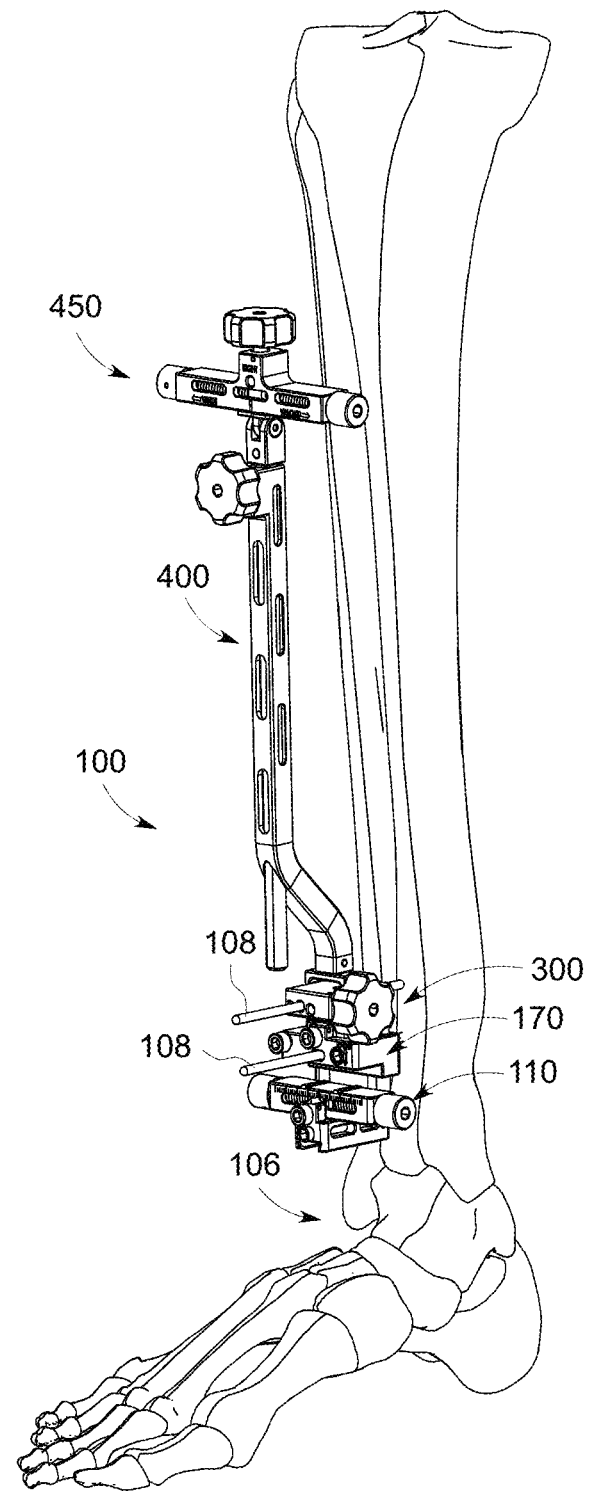
FIG. 27 is a first perspective view of the tibia alignment guide of FIG. 1 positioned on a patient's bones, in accordance with an aspect of the present disclosure.
Figure 28:
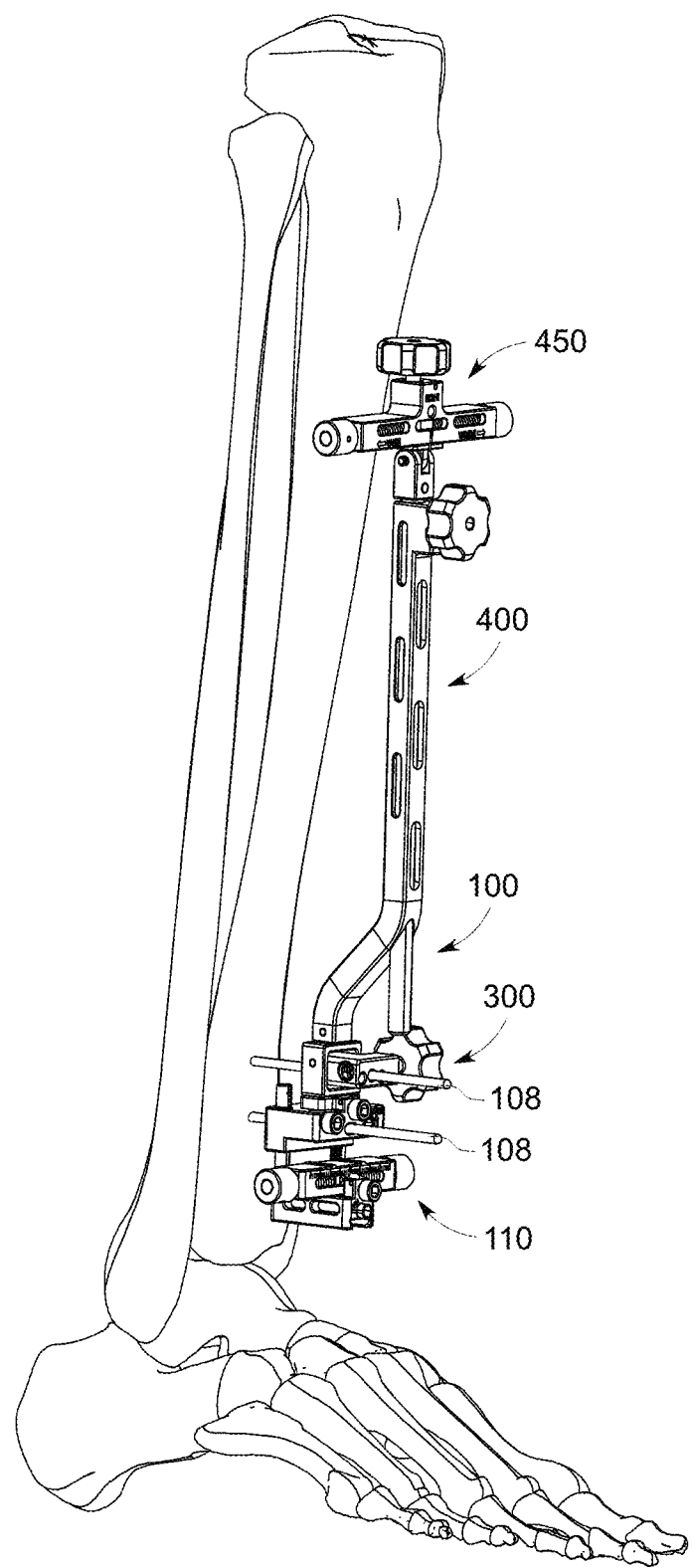
FIG. 28 is a second perspective view of the tibia alignment guide of FIG. 1 positioned on a patient's bones, in accordance with an aspect of the present disclosure.

Referring now to FIGS. 27-28, the alignment guide 100 is positioned on a patient's tibia 102 with at least two pins 108 and aligned with the ankle joint 106 to allow for a TAR procedure to be performed on the tibia 102 and the talus 104. At least one first pin 108 may be positioned at the distal end of the alignment guide 100 and extend through at least one of the first translation mechanism 110 and the second translation mechanism 170 and a second pin 108 (not shown) may be inserted through the third translation mechanism 300. Once positioned on the tibia 102, the first translation mechanism 110 may be used to achieve medial-lateral adjustment, the second translation mechanism 170 may be used to achieve distal-proximal adjustment, and the third translation mechanism 440 may be used to achieve varus-valgus adjustment. The surgical method may be as described in greater detail in U.S. Provisional Application No. 62/899,460, entitled Total Ankle Replacement Surgical Method, which is hereby incorporated by reference in its entirety.

Further although not shown, the alignment guide 100 may be coupled to various resection guides. The resection guides and resection instruments may be as described in greater detail in U.S. Provisional Application No. 62/898,615, entitled Resection Guides, Sweeping Reamers, and Methods for Use in Total Ankle Replacement, which is hereby incorporated by reference in its entirety. In addition, the alignment guide 100 may be used with additional instruments for the TAR procedure. The alignment guide 100 may be used with, for example, other alignment instruments such as a joint line pointer and additional alignment instruments, which are described in greater detail in U.S. Provisional Application No. 62/899,655, entitled Alignment Instruments and Methods for Use in Total Ankle Replacement, which is hereby incorporated by reference in its entirety.

Figure 29:
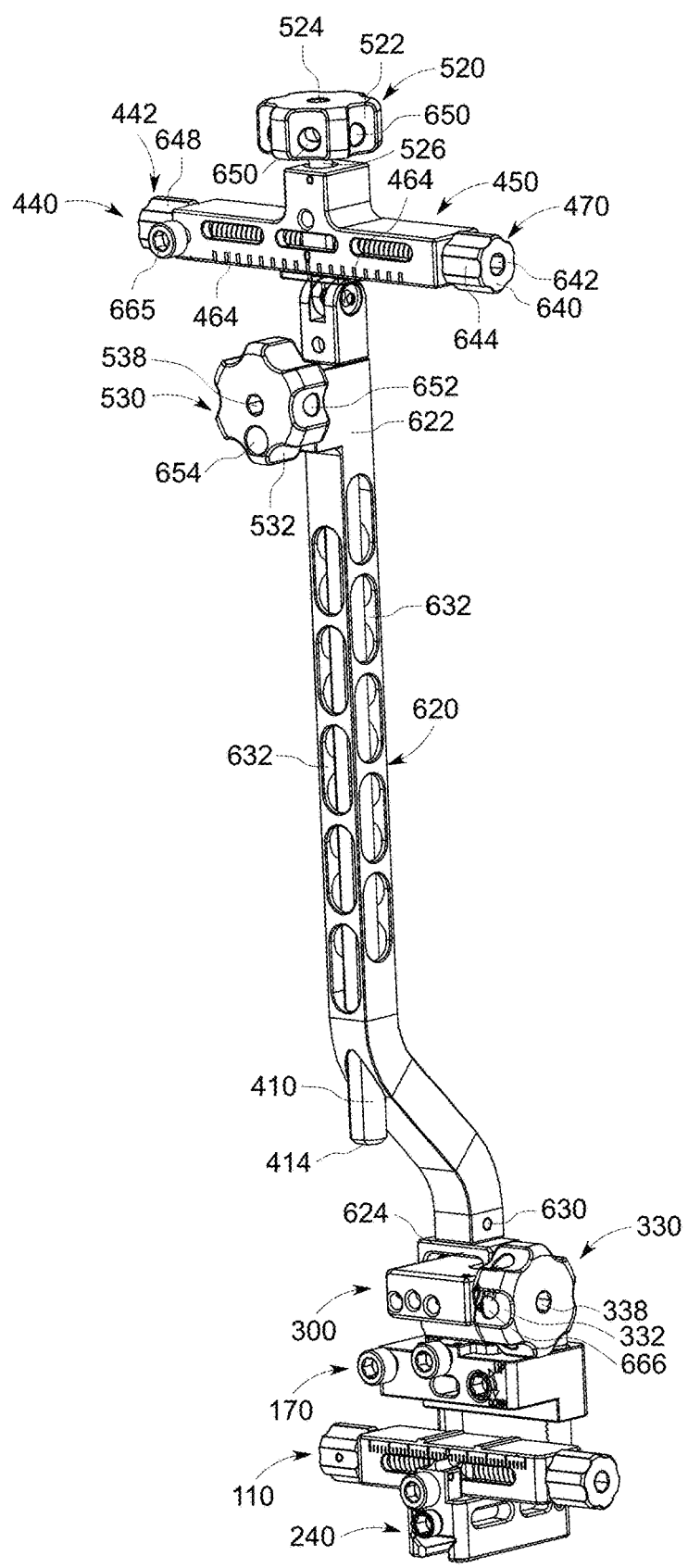
FIG. 29 is a first perspective view of another tibia alignment guide, in accordance with an aspect of the present disclosure.
Figure 30:
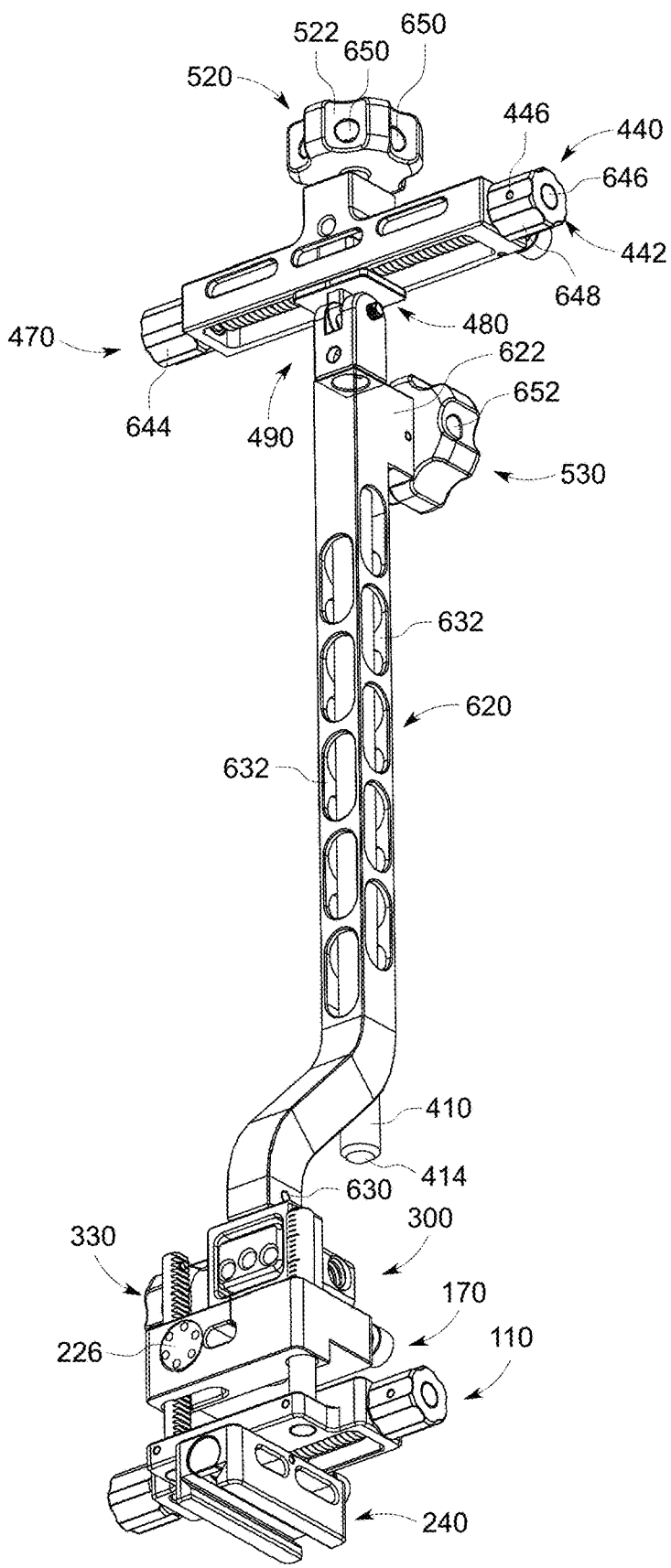
FIG. 30 is a second perspective view of the tibia alignment guide of FIG. 29, in accordance with an aspect of the present disclosure.
Figure 31:
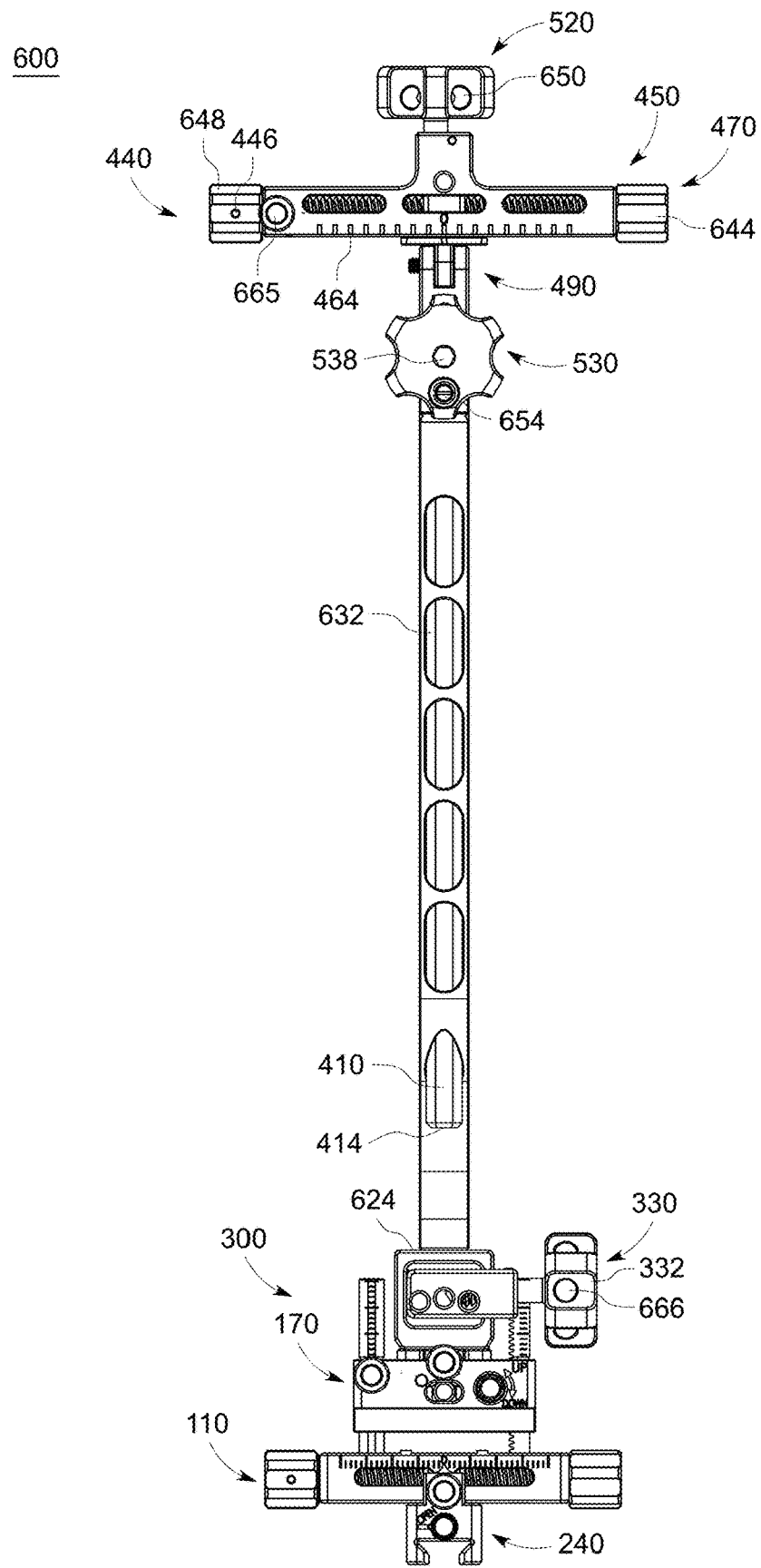
FIG. 31 is a first side view of the tibia alignment guide of FIG. 29, in accordance with an aspect of the present disclosure.
Figure 32:
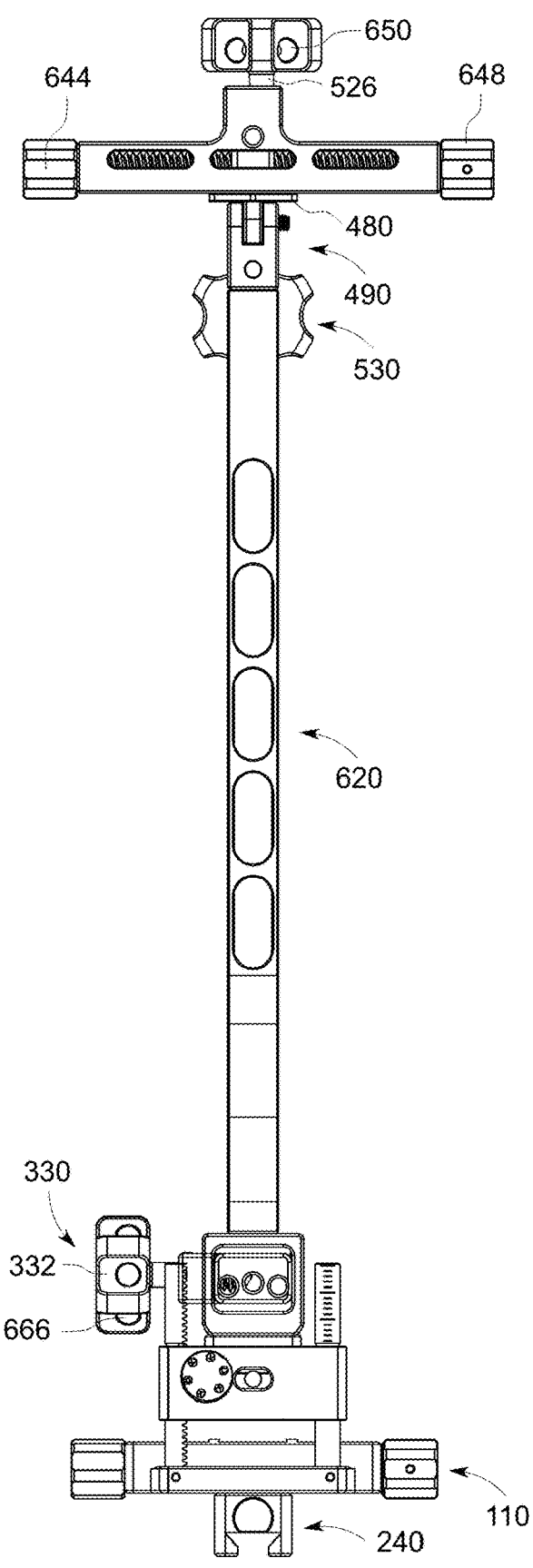
FIG. 32 is a second side view of the tibia alignment guide of FIG. 29, in accordance with an aspect of the present disclosure.
Figure 33:
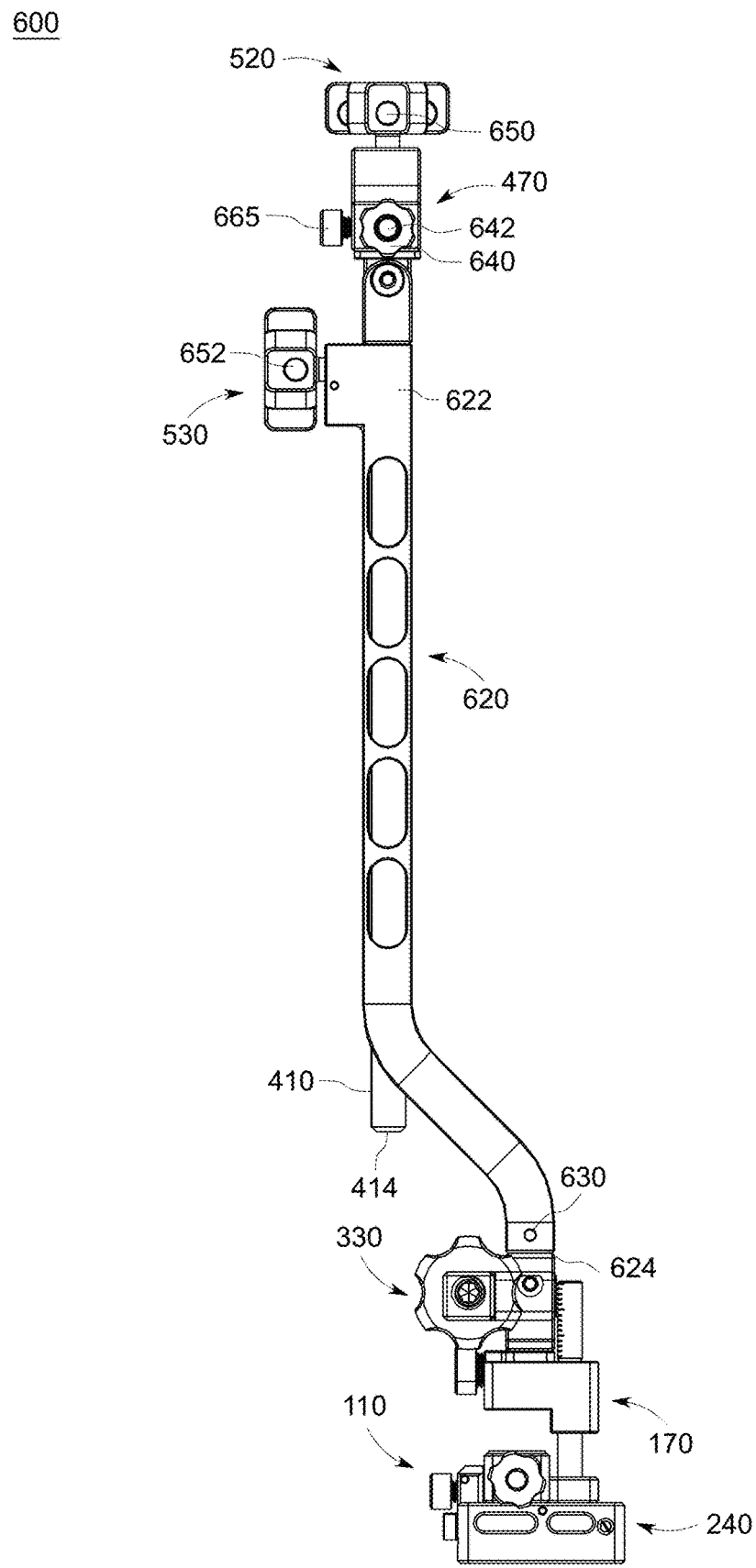
FIG. 33 is a first end view of the tibia alignment guide of FIG. 29, in accordance with an aspect of the present disclosure.
Figure 34:
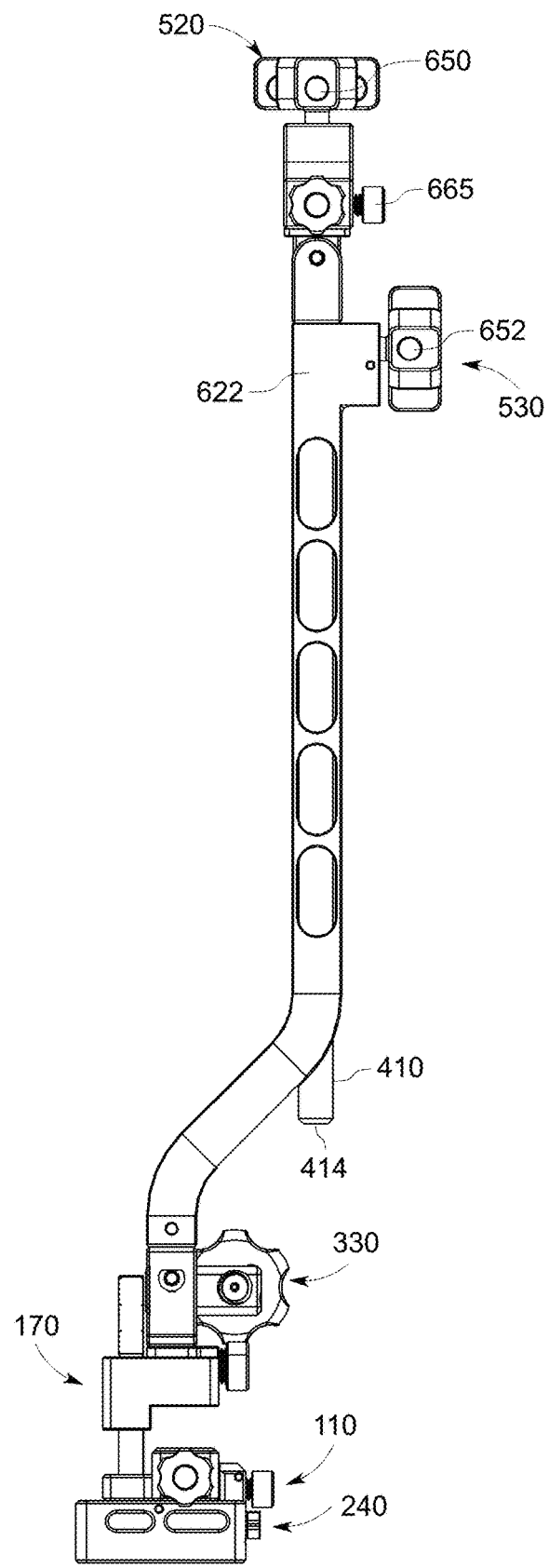
FIG. 34 is a second end view of the tibia alignment guide of FIG. 29, in accordance with an aspect of the present disclosure.
Figure 35:
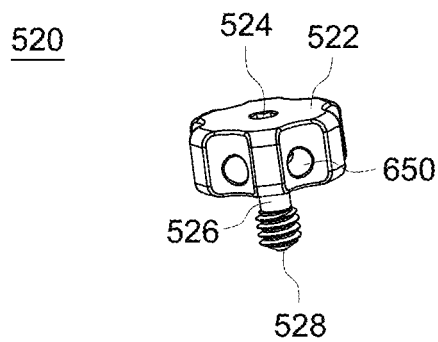
FIG. 35 is a perspective view of a third translation mechanism knob of the tibia alignment guide of FIG. 29, in accordance with an aspect of the present disclosure.

Referring now to FIGS. 29-39, another alignment guide or tibia alignment guide 600 is shown. The second alignment guide 600 may include components that are the same or similar to the first alignment guide 100, described in greater detail above. As shown in FIG. 29, the alignment guide or full alignment guide 600 includes a first translation mechanism or medial-lateral adjustment member 110, a second translation mechanism or distal-proximal adjustment member 170, a third translation mechanism or varus-valgus adjustment member 300, and a tower 620 coupled to the third translation mechanism 440 on a first end and the second translation mechanism 170 on a second end. The second translation mechanism 170 is movably coupled to the first translation mechanism 110 by distal-proximal translating members 150, 160. The third translation mechanism 440 is moveably coupled to the second translation mechanism 170 by the tower 620. The first and second translation mechanisms 110, 170 may be as described and shown in greater detail in U.S. Provisional Application No. 62/899,703, entitled Joint Replacement Alignment Guides, Systems and Methods of Use and Assembly, which is hereby incorporated by reference in its entirety.

Figure 36:
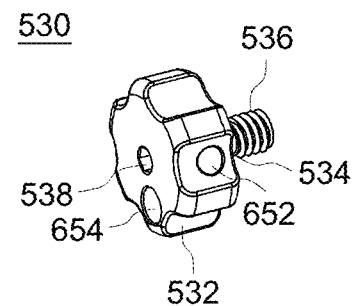
FIG. 36 is a perspective view of a tower system knob of the tibia alignment guide of FIG. 29, in accordance with an aspect of the present disclosure.

The tower 620 may be, for example, similar to the tower 420, as described in greater detail with respect to guide 100 and which will not be described again here for brevity sake. The tower 620 may include, for example, more windows or openings 632, as shown in FIGS. 29-34, than included in tower 420. Although not shown, the tower 620 also includes a first or threaded opening 426 and a second opening 428 for coupling the tower base 620 to the third translation mechanism 440. The threaded opening 426 may be, for example, sized and shaped or configured to receive a knob 530. The knob 530 may be, for example, the similar to knob 432. The knob 530 may include a head or drive portion 532 and a stem or shaft 534 extending away from a bottom surface of the head portion 532, as shown in FIG. 36. The shaft 534 may include a threaded portion 536 extending along at least a portion of the length of the shaft 534. The threaded portion 536 may be, for example, configured or sized and shaped to be inserted into the opening 426 in the tower 620. The locking knob 530 may also include a drive feature 538 inset into the first end of the head 532 of the knob 530. The locking knob 530 may further include at least one opening 652 extending into the head portion 532 from an exterior surface. The at least one opening 652 may be, for example, one or more openings 652 positioned around the circumference of the head portion 532. If two openings 652 are positioned on alternative sides of the head portion 532, the two openings 652 may form a through hole extending across the entire head portion 532. The at least one opening 652 may be, for example, sized and shaped or configured to receive a tool to assist with rotating the knob 530. The locking knob 530 may also include a recess 654 extending into the head portion 532 from a superior or top surface.

The alignment guide 600 may also include an alternative locking knob 520 and an alternative securement knob 330. As shown in FIGS. 29-35, the alternative locking knob 520 also includes at least one opening 650 extending into the head portion 522 from an exterior surface. The at least one opening 650 may be, for example, one or more openings 650 positioned around the circumference of the head portion 522. If two openings 650 are positioned on alternative sides of the head portion 522, the two openings 650 may form a through hole extending across the entire head portion 522. The at least one opening 652 may be, for example, sized and shaped or configured to receive a tool to assist with rotating the knob 530. The locking knob 530 may also include a recess 654 extending into the head portion 532 from a superior or top surface, as shown in FIG. 36.

Figure 39:
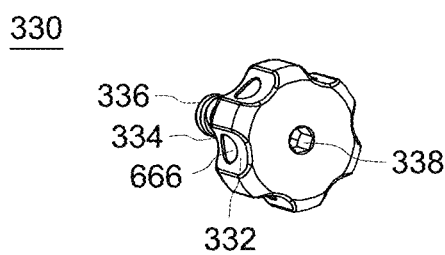
FIG. 39 is a perspective view of a coupling member knob of the tibia alignment guide of FIG. 29, in accordance with an aspect of the present disclosure.

The alternative securement knob 330 also includes at least one opening 666 extending into the head portion 332 from an exterior surface, as shown in FIG. 39. The at least one opening 666 may be, for example, one or more openings 666 positioned around the circumference of the head portion 332. If two openings 666 are positioned on alternative sides of the head portion 332, the two openings 666 may form a through hole extending across the entire head portion 332. The at least one opening 666 may be, for example, sized and shaped or configured to receive a tool to assist with rotating the knob 330.

Figure 37:
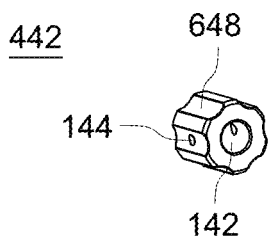
FIG. 37 is a perspective view of a third translation mechanism cap of the tibia alignment guide of FIG. 29, in accordance with an aspect of the present disclosure.
Figure 38:
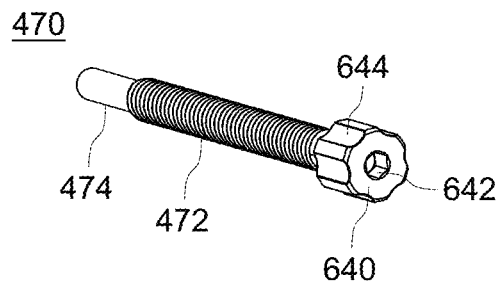
FIG. 38 is a perspective view of a third translation mechanism fastener of the tibia alignment guide of FIG. 29, in accordance with an aspect of the present disclosure.

The alignment guide 600 may also include an alternative head portion 640 of the fastening mechanism 470 and an alternative cap 442. As shown in FIG. 38, the head portion 640 of the fastening mechanism 470 may include a drive feature 642 extending into the head portion 640 from a first end. The head portion 640 may also include grooves 644 positioned around the circumference of the head portion 640. As shown in FIG. 37, the alternative cap 442 may also include grooves 644 positioned around the circumference of the head portion 442. The alignment guide 600 further includes a plurality of dimension markings 464 positioned along at least a portion of the first side of the housing 450 between the first end and the second end.

In addition, the alignment guide 600 may further include a locking knob 665. The locking knob 665 may be inserted into an opening (not shown) in housing 450. The opening may be positioned near a second end of the housing 450. The locking knob 665 may extend into at least one of the second opening 454 or cavity 456 to engage the fastening member 470. The locking knob 665 may, for example, engage the fastening member 470 to prevent further rotation once the desired position is achieved.

The above disclosure describes a portion of a total ankle replacement (TAR) procedure and the devices used in that procedure. Additional understanding of the TAR procedure may be found in U.S. Provisional Application No. 62/779, 436 filed Dec. 13, 2018 and entitled Joint Replacement Systems and Methods of Use and Assembly, International Application No. PCT/US2019/029009 filed Apr. 24, 2019 and entitled Implants and Methods of Use and Assembly, U.S. Provisional Application No. 62/779,092 filed Dec. 13, 2018 and entitled Instruments, Guides and Related Methods for Total Ankle Replacement, International Application No. PCT/US2019/066404 filed Dec. 13, 2019 and entitled Instruments, Guides and Related Methods for Total Ankle Replacement, U.S. Provisional Application No. 62/890,611 filed Aug. 22, 2019 and entitled Patient Specific Instruments and Methods of Use, International Application No. PCT/US2019/066336 filed Dec. 13, 2019 and entitled Patient Specific Instruments and Methods of Use, U.S. Provisional Application No. 62/899,703 filed Sep. 12, 2019 and entitled Joint Replacement Alignment Guides, Systems and Methods of Use and Assembly, International Application No. PCT/US2019/066408 filed Dec. 13, 2019 and entitled Joint Replacement Alignment Guides, Systems and Methods of Use and Assembly, U.S. Provisional Application No. 62/899,655 filed Sep. 12, 2019 and entitled Alignment Instruments and Methods for Use in Total Ankle Replacement, International Application No. PCT/US2019/066149 filed Dec. 13, 2019 and entitled Alignment Instruments and Methods for Use in Total Ankle Replacement, U.S. Provisional Application No. 62/899,740 filed Sep. 12, 2019 and entitled Joint Replacement Alignment Guides, Systems and Methods of Use and Assembly, U.S. Provisional Application No. 62/898,615 filed Sep. 11, 2019 and entitled Resection Guides, Sweeping Reamers, and Methods for Use in Total Ankle Replacement, International Application No. PCT/US2019/064948 filed Dec. 6, 2019 and entitled Resection Guides, Sweeping Reamers, and Methods for Use in Total Ankle Replacement, U.S. Provisional Application No. 62/898,854 filed Sep. 11, 2019 and entitled Distractors Having Attachable Paddles, Impaction Devices, and Methods for Use in Total Ankle Replacement, International Application No. PCT/US2019/066398 filed Dec. 13, 2019 and entitled Distractors Having Attachable Paddles, Impaction Devices, and Methods for Use in Total Ankle Replacement, U.S. Provisional Application No. 62/899,646 filed Sep. 12, 2019 and entitled Trial Insert Assembly, International Application No. PCT/US2019/065025 filed Dec. 6, 2019 and entitled Trial Insert Assembly, U.S. Provisional Application No. 62/899,460 filed Sep. 12, 2019 and entitled Total Ankle Replacement Surgical Method, International Application No. PCT/US2019/066409 filed Dec. 13, 2019 and entitled Total Ankle Replacement Surgical Method, which are each hereby incorporated herein in their entireties.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. For example, the components and features of FIGS. 1-28 and FIGS. 29-39 may be used interchangeably and in alternative combinations as would be modified or altered by one of skill in the art. Specifically, alignment guides 100, 600 may be used in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A method of assembling an alignment guide system, comprising:
   obtaining a first translating mechanism, a second translating mechanism, a third translating mechanism, and a tower system;
   coupling the first translating mechanism to the second translating mechanism;
   coupling the tower system to the second translating mechanism; and
   coupling the third translating mechanism to the tower system;
   wherein the first translating mechanism comprises:
      a housing having first and second sides, the housing comprising:
         a first opening extending into the housing from a first end;
         a second opening extending into the housing from a second end;
         a cavity extending into the housing from a distal surface, wherein the first opening, the second opening, and the cavity overlap; and
         an extension member extending away from the second side of the housing;
      a fastening member extending through at least a portion of the housing; and
      a cap secured to a portion of the fastening member.

2. The method of claim 1, further comprising assembling the first translating mechanism.

3. The method of claim 2, wherein assembling the first translating mechanism comprises inserting a translating protrusion into a channel of a base of the first translating mechanism.

4. The method of claim 3, wherein assembling the first translating mechanism further comprises inserting a securement fastener through a first through hole to engage a first side of the housing.

5. The method of claim 4, wherein assembling the first translating mechanism further comprises inserting a drive member at least partially into a second through hole and inserting an engagement pin at least partially into an engagement pin hole such that the engagement pin engages a groove in the drive member.

6. The method of claim 5, wherein assembling the first translating mechanism further comprises inserting the fastening member into the first opening.

7. The method of claim 6, wherein the fastening member is positioned to extend through the cavity and a third through hole of a translating protrusion such that at least a portion of the fastening member extends out of the second opening.

8. The method of claim 7, further comprising inserting a pin at least partially into a first locking opening of a coupling member and through a second locking opening of the fastening member such that a threaded portion of a shaft portion of the fastening member is retained within the cavity of the housing.

9. The method of claim 8, further comprising:
inserting a distal end of the first translating mechanism into a first recess; and
inserting a first locking member through the extension member and into the first opening of the first translating mechanism such that the first translating mechanism is secured to the extension member of the housing.

10. The method of claim 9, further comprising:
inserting a distal end of the second translating member at least partially into a second recess; and
inserting a second locking member at least partially through the extension member and the second opening of the second translating member such that the second translating member is releasably coupled with the housing of the first translating mechanism.

11. The method of claim 10, further comprising aligning the second translating mechanism with the first translating mechanism and the second translating member.

12. The method of claim 11, wherein:
the first translating mechanism is received within the cavity of the housing; and
an engagement member of the second translation mechanism comprises a plurality of teeth configured to translatably engage a second plurality of teeth of the housing such that the housing is manipulatable with respect to the coupled first translating mechanism and the coupling member.

13. The method of claim 11, further comprising:
positioning the engagement member within the cavity; and
rotatably coupling the drive member with the engagement member such that the drive member is rotatably translatable with respect to the engagement member.

14. The method of claim 13, further comprising:
inserting a locking cap within a locking cap opening of the second translating member such that the locking cap engages the drive member such that the engagement member is retained within the cavity.

15. The method of claim 14, further comprising:
inserting the second translating member into a fourth through hole when a locking fastener is positioned in either a locked or unlocked position.

16. The method of claim 15, wherein the locking fastener is manipulatable so as to secure the second translating member in a desired position in distal-proximal directions.

17. A method of using an alignment guide system, comprising:
obtaining the alignment guide system comprising:
a first translating mechanism, wherein the first translating mechanism comprises:
a housing having first and second sides, the housing comprising:
a first opening extending into the housing from a first end;
a second opening extending into the housing from a second end;
a cavity extending into the housing from a distal surface, wherein the first opening, the second opening, and the cavity overlap; and
an extension member extending away from the second side of the housing;
a fastening member configured to be received at least partially within and extending through at least a portion of the housing; and
an engagement member comprising a plurality of teeth configured to translatably engage a second plurality of teeth of the housing such that the housing is manipulatable with respect to the coupled first translating mechanism and coupling member;
a second translating mechanism coupled with the first translating mechanism;
a tower coupled to a superior surface of the second translating mechanism; and
a third translating mechanism coupled to the tower;
coupling the alignment guide system to a tibia of a patient; and
translating the alignment guide system in at least one of a medial-lateral, a distal-proximal, and a *varus*-valgus direction.

18. The method of claim 17, further comprising:
releasably coupling a pair of pins with the alignment guide system and the tibia of the patient so as to releasably couple the alignment guide system with the tibia of the patient.

* * * * *